(12) United States Patent
Berd et al.

(10) Patent No.: US 8,435,784 B2
(45) Date of Patent: May 7, 2013

(54) CRYOPRESERVATION OF HAPTENIZED TUMOR CELLS

(76) Inventors: David Berd, Wyncote, PA (US); Lorne F. Erdile, Loudonville, NY (US); Margalit B. Mokyr, Skokie, IL (US)

(*) Notice: Subject to any disclaimer, the term of this patent is extended or adjusted under 35 U.S.C. 154(b) by 1068 days.

(21) Appl. No.: 11/762,409

(22) Filed: Jun. 13, 2007

(65) Prior Publication Data

US 2007/0237795 A1 Oct. 11, 2007

Related U.S. Application Data

(63) Continuation of application No. 11/009,192, filed on Dec. 9, 2004, now abandoned, which is a continuation of application No. PCT/US03/18310, filed on Jun. 10, 2003.

(60) Provisional application No. 60/387,660, filed on Jun. 10, 2002.

(51) Int. Cl.
| | | |
|---|---|---|
| *A01N 1/00* | (2006.01) | |
| *A01N 1/02* | (2006.01) | |
| *C12N 5/00* | (2006.01) | |
| *C12N 5/02* | (2006.01) | |
| *C12N 5/07* | (2010.01) | |
| *C12N 5/16* | (2006.01) | |
| *G01N 33/574* | (2006.01) | |

(52) U.S. Cl.
USPC ............ 435/325; 435/1.3; 435/7.23; 435/345

(58) Field of Classification Search .................. None
See application file for complete search history.

(56) References Cited

U.S. PATENT DOCUMENTS

| | | | |
|---|---|---|---|
| 5,290,551 | A | 3/1994 | Berd |
| 5,478,556 | A | 12/1995 | Elliott et al. |
| 5,484,596 | A | 1/1996 | Hanna, Jr. et al. |
| 5,550,214 | A | 8/1996 | Eberlein et al. |
| 6,248,585 | B1 | 6/2001 | Berd |
| 6,333,028 | B1 | 12/2001 | Berd |

FOREIGN PATENT DOCUMENTS

| | | |
|---|---|---|
| WO | WO 96/40173 | 12/1996 |
| WO | WO 98/14206 | 4/1998 |
| WO | WO 99/40925 | 8/1999 |
| WO | WO 99/52546 | 10/1999 |
| WO | WO 99/56773 | 11/1999 |
| WO | WO 00/09140 | 2/2000 |
| WO | WO 00/29554 | 5/2000 |
| WO | WO 00/31542 | 6/2000 |
| WO | WO 00/38710 | 7/2000 |

*Primary Examiner* — Debbie K Ware

(74) *Attorney, Agent, or Firm* — Morgan, Lewis & Bockius LLP

(57) ABSTRACT

A method of preserving haptenized tumor cells is described. The method employs a freezing medium containing an effective amount of sucrose and human serum albumin in an isotonic buffered saline solution. Cryogenically preserving haptenized cells in such a medium has been found to maintain the integrity of the tumor cells during storage. The haptenized tumor cells also retain cell-associated antigens and haptens, and are as immunogenic, i.e., capable of inducing immunotherapeutic response, as fresh vaccine in a mouse model of metastatic disease. In a specific embodiment, haptenized cells are exposed to a solution of 8% sucrose, 10% human serum albumin in Hank's buffered solution, and then frozen to −80° C. overnight and then stored in a liquid nitrogen freezer. Methods of storing haptenized tumor cells and compositions are also provided.

12 Claims, 4 Drawing Sheets

US 8,435,784 B2

CRYOPRESERVATION OF HAPTENIZED TUMOR CELLS

CROSS-REFERENCE TO RELATED APPLICATIONS

This application is a continuation of U.S. patent application Ser. No. 11/009,192 filed Dec. 9, 2004, now abandoned, which is a continuation of International Patent Application No. PCT/US03/018310 filed Jun. 10, 2003, which claims priority to U.S. Provisional Application No. 60/387,660 filed Jun. 10, 2002, all of which are incorporated herein by reference in their entirety.

FIELD OF THE INVENTION

The invention relates to compositions and methods for cryo-preservation of haptenized tumor cells. The rumor cell compositions are particularly suitable for an immunotherapeutic vaccine.

BACKGROUND OF THE INVENTION

In blood transfusion, bone marrow transplantation, immuno-therapeutic vaccine preparation, or other cell preparations ex vivo, one of the principal problems encountered is that of the preservation of cells. It is critical to be able to preserve cells, under good conditions of viability, for time periods compatible with clinical production and storage, and to make it possible to analyze cell preparations. The most commonly used method of long-term preservation of cells is to freeze and subsequently thaw them. However, during the freezing of cells, lysis of cells and loss of cell integrity may occur. This is often observed by the decrease in intact tumor cells and the concomitant increase in the amount of non-intact tumor cells in a sample of tumor cells. This problem can be even more complex when the cells have been modified or altered prior to preservation, and when the cells are obtained by proteolytic digestion of a tissue or tumor specimen. Preservation of cells under less extreme conditions, for example on ice (about 0° C.), refrigerated (about 4° C.), or at room temperature, prior to use, is also difficult as these storage conditions are effective only for a period of hours.

Immunotherapy

The preservation of cells, especially their immunogenicity, is important is in immunotherapy of cancer using tumor cells. The aim of the immunotherapy is to evoke an immune response to the tumor, or to vaccinate against new tumors, by administering tumor cells or tumor cell extracts to the cancer patient. The tumor cells in the composition should contain antigens that are also present in the tumor to be treated, so that the immune response elicited against the antigens in the composition is effective against the tumor. Generally, the cells are recovered from tumors, suspended in a cryopreservation medium and frozen until used for the vaccine preparation. When needed, the cells are thawed, and then stored at temperatures ranging from about 0° C. (on ice) to room temperature until administration.

Immunotherapy regimens using unmodified intact tumor cells prepared from tumors taken from the patient, i.e., autologous tumor cells, have been extensively described in the literature (see, e.g., Berd et al., Cancer Research 1986; 46:2572-2577; Hoover et al., Cancer 1985; 55:1236-1243; and U.S. Pat. No. 5,484,596 to Hanna et al.). Alternative vaccine compositions based on disrupted cells have also been suggested including, e.g., tumor membranes (see, e.g., Levin et al., In: Human Tumors in Short Term Culture: Techniques and Clinical Applications, P. P. Dendy, Ed., 1976, Academic Press, London, pp. 277-280) or tumor peptides extracted from tumors (see, e.g., U.S. Pat. No. 5,550,214 to Eberlein, and U.S. Pat. No. 5,487,556 to Elliot et al.). The tumor cells can also be modified in some manner to alter or increase the immune response (see, e.g., Hostetler et al., Cancer Research 1989; 49:1207-1213; and Muller et al., Anticancer Research 1991; 11:925-930).

Haptenized Tumor Cell Vaccines

One particular form of tumor cell modification that has a pronounced effect on immunotherapy is coupling of a hapten to the tumor cells. An autologous whole-cell vaccine modified with the hapten dinitrophenyl (DNP) has been shown to produce inflammatory responses in metastatic sites of melanoma patients. Adjuvant therapy with DNP-modified vaccine produces markedly higher post-surgical survival rates than those reported after surgery alone. U.S. Pat. No. 5,290,551 to Berd discloses and claims vaccine compositions comprising haptenized melanoma cells. Melanoma patients who were treated with these cells developed a strong immune response. This response can be detected in a delayed-type hypersensitivity (DTH) response to haptenized and non-haptenized tumor cells. More importantly, the immune response resulted in increased survival rates of melanoma patients.

Haptenized tumor cell vaccines have also been described for other types of cancers, including lung cancer, breast cancer, colon cancer, pancreatic cancer, ovarian cancer, and leukemia (see International Patent Publication Nos. WO 96/40173 and WO 00/09140, and U.S. Pat. No. 6,333,028, and the associated techniques and treatment regimens optimized (see International Patent Publication Nos. WO 00/38710, WO 00/31542, WO 99/52546, and WO 98/14206). For example, it has been shown that the addition of human serum albumin (HSA) increases the stability of haptenized tumor cell preparations (see WO 00/29554 and U.S. Pat. No. 6,248,585).

It has also been found that haptenization of tumor cell extracts such as plasma membranes and peptides can yield potent immunotherapy vaccines (see International Patent Publication Nos. WO 96/40173 and WO 99/40925, both by Berd et al.).

For haptenized vaccines, the search for storage conditions that preserve the stability of the haptenized cells or extracts also have to take into account that some haptenization reactions may alter or affect the cell viability or integrity. Previous work has suggested that if no measures are taken to increase the stability of haptenized melanoma vaccine preparations, they might have a cell integrity duration of less than four hours after hapten modification. Also, some haptens or haptenization procedures render the cells more fragile than others. For example, while preparations of DNP-modified cells can be stable for at least 18 hours when stored at 4° C., some procedures for sulfanilic acid (SA) conjunction render the cells more fragile, and the SA-modified cells may in some cases only be stable for less than 2 hours at 4° C.

However, whether utilizing modified or unmodified tumor cells, in order to elicit a successful immune response against the tumors of the patient after administration, the amount and immunogenicity of the antigens in the tumor cell composition should be retained as much as possible during preparation and storage of the composition. The tumor antigens should also remain associated with the cells.

Thus, there is a need in the art for an effective treatment for cells to be stored and preserved prior to delivery as an immunotherapy vaccine. There is also a need for a treatment that preserves the integrity, antigen-content and immunogenicity of such cells for vaccines prior to administration, and methods for designing tumor cell preparations and formulations to obtain optimal immune response. The present invention advantageously addresses these and other needs in the art.

SUMMARY OF THE INVENTION

The present invention is based, in part, on a cryopreservation method found to preserve a haptenized tumor cell vaccine in terms of the number of intact tumor cells; the density of various tumor-cell associated antigens, including haptens; and the in vivo immunogenicity and immunotherapeutic potential of the tumor cell vaccine. The present invention therefore advantageously provides a method of treating tumor cells or tumor cell extracts for their preservation and/or storage prior to use in anti-tumor vaccines.

Accordingly, the invention provides a method of preserving haptenized tumor cells, which method comprises: (i) contacting the haptenized tumor cells with a freezing medium, wherein the freezing medium comprises sucrose, human serum albumin and an isotonic buffered solution; and (ii) freezing the tumor cells, whereby the immunogenicity of the tumor cells is preserved. In one embodiment, the isotonic buffered saline solution is Hank's buffered solution. For example, the freezing medium may comprise an 8% sucrose, 10% human serum albumin-supplemented Hank's buffered solution. The storage temperature can be from about −20° C. to about −196° C., preferably −80° C. to about −196° C. In one embodiment, at least 70%, preferably at least 90%, of the level of at least one tumor cell-associated antigen (TCAA) is preserved after about 3 months storage at a temperature, e.g., of −80° C. or less. In another embodiment, at least 50%, preferably at least 70%, of the haptenized tumor cells are preserved intact after about 3 months storage, e.g., at a temperature −80° C. or less. The tumor cells may, for example, be melanoma cells, ovarian cancer cells, colorectal cancer cells, small cell lung cancer cells, kidney cancer cells, breast cancer cells, or leukemia cells. In a particular embodiment, the tumor cells are melanoma cells. The tumor cells are haptenized with at least one hapten, which can be selected from, e.g., DNP, TNP, and sulfanilic acid. In a particular embodiment, the hapten is DNP. In another particular embodiment, the tumor cells are haptenized with at least two different haptens.

The invention also provides for a method of storage for haptenized tumor cells for use in a vaccine, which method comprises storing a haptenized tumor cells and freezing medium composition at a temperature below the freezing temperature for at least 3 months. In one embodiment, the temperature is from about −80° C. to −196° C. The tumor cells may be haptenized with, for example, at least one hapten selected from DNA and sulfanilic acid.

The invention also provides for a composition comprising haptenized tumor cells for use in a vaccine and freezing medium, wherein the freezing medium comprises sucrose, human serum albumin and an isotonic buffered saline solution. Preferably, the freezing medium comprises 8% sucrose, 10% human serum albumin and the isotonic buffered saline solution is Hank's buffered solution. The tumor cells can be, for example, melanoma cells, ovarian cancer cells, colorectal cancer cells, small cell lung cancer cells, kidney cancer cells, breast cancer cells, or leukemia cells. In a particular embodiment, the tumor cells are melanoma cells. The tumor cells are haptenized with at least one hapten, which can be selected from, e.g., DNP, TNP, and sulfanilic acid. In a particular embodiment, the hapten is DNP. In another particular embodiment, the tumor cells are haptenized with at least two different haptens.

The Drawings, Detailed Description, and Examples will further explain the present invention.

DETAILED DESCRIPTION OF THE INVENTION

Figure 1:
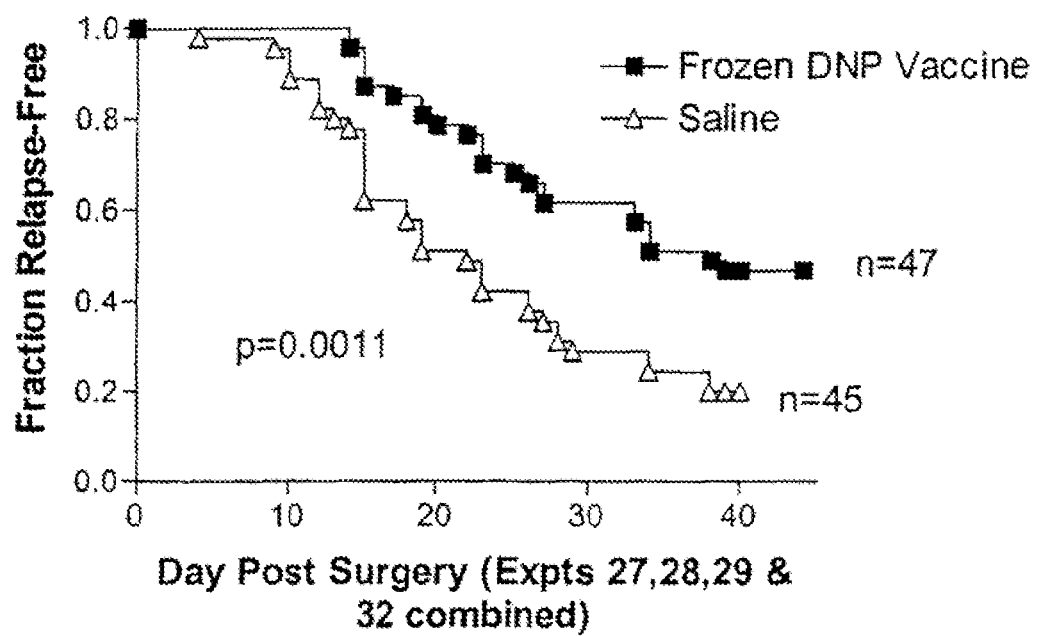
FIG. 1 shows the relapse-free survival rate of mice after surgical removal of primary 410.4 mammary adenocarcinoma tumors and treatment with cryogenically preserved irradiated DNP-modified tumor cells as compared to control mice treated with saline.

The present invention advantageously provides a new cryopreservation method that stabilizes haptenized tumor cells or tumor cell extracts for storage and maintains immunogenicity, the level of cell-associated antigens, and/or the integrity of the tumor cells. Provided are also compositions formed by such a method. Advantages of the present method include that the method allows for storing tumor cells for months after preparation without risking substantial loss of intact cells, cell-associated antigens, and/or immunogenicity. For example, the cryopreservation method may not result in any significant loss of the density of various tumor cell associated antigens (TCAA). The preserved tumor cells are sufficiently immunogenic to provide protective immunity, and may retain the same immunogenicity, as assessed by an in vivo assay, as a fresh preparation of the same type of tumor cells. Thus, the method of the invention provides an additional time window during which a tumor cell composition may be shipped to a clinic, examined for quality control, or subjected to further manipulation or analysis, prior to patient administration as a vaccine.

The method for the preservation and/or storage of tumor cells comprises contacting the cells with a freezing medium comprising an effective amount of sucrose and human serum albumin, and then freezing the cells. The cells can be stored at any temperature below the freezing temperature of the composition. Non-limiting examples of storage temperatures include below −10° C., preferably below −20° C., even more preferably below −80° C. Particularly preferred temperatures are in the range from about −80° C. to about −196° C. Suitable storage medial includes liquid nitrogen and freezers capable of maintaining suitable temperatures. The cryopreservation method of the invention is suitable for treatment of, e.g, any haptenized tumor cell such as, e.g., haptenized tumor cells derived from melanoma, ovarian cancer, small cell lung cancer, colon cancer, leukemia, or lymphoma, or haptenized membrane extracts of such tumor cells.

It has been found that preserved haptenized tumor cells that have been treated with freezing medium and cryopreserved by the method of the present invention can be utilized in vaccines due to their retention of cell characteristics and preservation of surface haptenization, such as DNP, and antigens such as MHC1, even if the cells do not exclude trypan blue. Preferably, in a solution of freezing medium treated cells that are frozen to about −196° C., more than 50%, preferably at least 60%, and even more preferably at least 70% of the tumor cells remain intact, and more than 50% preferably more than 80%, and even more preferably more than 90% of a tumor cell-associated antigen is preserved (present on the cells) after storage. Although the cells may be stored for any suitable period of time, it is preferred that the tumor cells be stored for up to 3 months. In a specific embodiment, the tumor cells are human tumor cells.

The freezing medium of the present invention is a composition comprising an effective amount of sucrose and human serum albumin and an isotonic buffered saline solution to stabilize the haptenized tumor cells and preserve the antigenicity of the haptenized tumor cells during the freezing process. In a preferred embodiment, the freezing medium is composed of sucrose, human serum albumin and Hanks solution. The use of sucrose and human serum albumin and an isotonic buffered saline solution in the freezing medium preserves one or more of the antigenicity, immunogenicity and stability during cryopreservation while maintaining the ability of the vaccine to be used in humans. By contrast, other freezing medium additives are not usable with haptenized tumor cell vaccines. For example, the use of dextran in the freezing medium in a cryopreserved haptenized tumor cell vaccine resulted in a vaccine that was unusable in human as it induced anaphylaxis in mice.

In the present invention, the sucrose content preferably ranges from about 0.1% to about 40%. More preferably, the sucrose content ranges from about 1% to about 20%. Even more preferably, the sucrose content ranges from about 5% to about 15%. Most preferably, the sucrose content is about 8%.

In addition to sucrose, the freezing medium can comprise human serum albumin and an isotonic buffered saline solution. Preferably, the humans serum albumin content ranges from about 1% to about 30%. More preferably, the human serum albumin content ranges from about 5% to about 15%. Even more preferably, the human serum albumin content is about 10%. Hanks buffered solution or HBSS, a well-known buffer solution, is discussed in more detail below.

In a preferred embodiment, Hanks buffered solution is included as an isotonic buffered saline in the freezing medium. The skilled artisan will understand that other buffered salt solutions may be utilized, for example PBS. The formulations section, below, lists non-limiting examples of buffered salt solutions. A preferred freezing medium of the invention is a composition that comprises about 8% sucrose and about 10% human serum albumin in Hanks solution.

It will be appreciated by one skilled the art that the freezing process includes the reduction of the temperature of the sample to the desired temperature, the maintenance of the desired temperature during storage of the sample, and thawing the sample for further use as a vaccine. Depending on the type of tumor cells, e.g., from different types of cancers, and the intended use, there may be variations as to the temperature reduction rate and other parameters. Based on the present disclosure, such parameters are easily recognized by a person skilled in the art, who can optimize stability and preservation of antigenicity to suit desired storage and sample conditions. In addition, the levels of purity and sterility for each intended use can be determined, and the preparation and freezing process optimized accordingly. While the haptenized tumor cells may be brought into contact with the freezing medium by any suitable method, suspending the haptenized tumor cells in the freezing medium is preferred.

The cryopreservation or freezing of haptenized tumor cells occurs when the haptenized tumor cells and freezing medium mixture is reduced in temperature relative to the temperature at which the freezing medium and haptenized tumor cells were contacted. Preferably, the temperature of the mixture is reduced to about −20° C., and then to about −196° C., and maintained at such temperature for the length of the desired storage. The longer the desired storage time, the lower the storage temperature should be utilized to improve yield. The haptenized tumor cells are preferably stored in freezing medium at about −196° C., especially for long term storage. For short and medium time periods, higher storage temperatures can also be used. Preferably, temperatures above about −80° C. are not utilized for medium term and short term storage. For short-term storage, the storage temperature is preferably not above −10° C., even more preferably not above about −20° C.

The temperature can be maintained by any method known in the Non-limiting examples of freezing methods include electric freezers that can maintain temperatures from about −20° C. to about −180° C. Such freezers are commercially available. One such supplier is TermaForma of Marietta, Ohio. In addition, freezers can maintain ultra-cold temperatures by non-electric methods, which is also known in the art. For example, dry ice (frozen carbon dioxide at about −78° C.) can be used to maintain cold temperatures. Another example is liquid nitrogen (−196° C.) that is commonly used in ultra-cold freezers. Ultra-cold freezers are commercially available, for example, from TermaForma of Marietta, Ohio. In a preferred embodiment of the invention, the sample is frozen overnight in a −80° C. freezer an then transferred to a liquid nitrogen freezer for storage. The storage time periods may extend for many months, e.g., for up to 9 months, preferably up to 6 months, and even more preferably for up to 3 months. Storage for days or weeks is also encompassed in the method of the invention.

After cryopreservation, the cells may be used for preparing a tumor cell vaccine for administration to a patient in need thereof. The preservation method of the invention is particularly advantageous for such applications, since preserved cell can be maintained a longer time in storage without losing cell-associated antigens, immunogenicity or vaccine potency, thus permitting a longer period of time for quality assurance (QA) and quality control (QC) of the vaccine before administration to the patient. After thawing the cryopreserved vaccine, it may be used for various therapeutic applications in patients, including immunoprotection (treatment prior to tumor development, i.e., "vaccination" against a tumor) and immunotherapy (treatment of a patient already suffering from a tumor to prevent, e.g., tumor recurrence or metastatic disease).

Haptenized tumor cells treated with the optimized concentration of freezing medium, comprising an effective amount of sucrose and human serum albumin and then cryopreserved at about −20° C. to about −196° C. substantially retain their cell characteristics and substantially preserve surface haptenization cell-associated antigens, as determined by flow cytometry. Preferably, the preservation of freezing-medium treated frozen cells is greater than the preservation of the same kind, number, and concentration of tumor cells contacted with a control medium for the same period of time and at the same temperature and then frozen for the same amount of time and at the same temperature.

The various aspects of the invention will be set forth in greater detail in the following sections, directed to suitable medium and formulations for preserving haptenized tumor cells.

Definitions

The following defined terms are used throughout the present specification, and should be helpful in understanding the scope and practice of the present invention.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

A "formulation" refers to an aqueous medium or solution for the preservation of haptenized tumor cells, which is preferably directly injectable into an organism. An aqueous buffer will include salts or sugars, or both, at about an isotonic concentration. The formulation may further comprise sucrose, as described herein.

"Human serum albumin" or "HSA" refers to a non-glycosylated monomeric protein consisting of 585 amino acid residues, with a molecular weight of 66 kD. Its globular structure is maintained by 17 disulphide bridges, which create a sequential series of 9 double loops (Brown, "Albumin structure, function and uses", Rosenoer, V. M. et al. (eds.), Pergamon Press:Oxford, pp. 27-51, 1977). HSA may also be called human plasma albumin.

A "live" cell means a cell that has an intact cell, plasma, or "outer" membrane as assessed by Trypan Blue exclusion. A live cell may be capable of growth or maintenance, and division or multiplication, or attenuated, i.e., incapable of division and multiplication. A cell can be rendered attenuated by, for example, irradiation.

"Dead" cells mean cells that do not exclude Trypan Blue as assessed in a Trypan Blue exclusion experiment, and that are incapable of division or multiplication. A "dead" cell can be prepared by, e.g., freezing a live cell. A dead cell appears intact, e.g., by microscopic inspection, meaning that the cellular shape resembles that of a live cell. A "fixed" cell is one example of a dead cell.

A "lysed" cell is no longer intact, meaning that the cellular shape does not resemble that of a live cell.

A "reserved" cell is a cell that is not lysed. A preserved cell can be live or dead. The cell may or may not exclude Trypan Blue, but retains its level of cell-associated antigens, preferably antigens present in the cell membrane, or its immunogenicity over time better than a cell that is not similarly preserved.

"Immunogenicity" means the ability of a tumor cell or tumor cell extract to evoke an immune response directed to the tumor cell or extract. Generally, immunogenicity is higher for a tumor cell in which the immunogenic molecules are intact. Whether a haptenized tumor cell preparation is immunogenic can be tested by, for instance, a DTH-assay or an in vivo assay in an experimental animal model. The animal model described in Example 5 demonstrates testing of human melanoma vaccines, and similar models can be applied for other tumor vaccines. Preservation of immunogenic molecules on tumor cells stored in accordance with the invention can be determined by direct measurement of the immunogen, or indirectly by measuring preservation of other tumor associated molecules, which should correlate with preservation of the immunogen.

A "tumor cell associated antigen" (TCAA; also referred to as a tumor associated antigen or "TAA") is an antigen associated with a tumor cell in such a manner that an antibody or another component of a mammalian immune system can recognize it. Preferably, although not necessarily, the TCAA is associated with the outer cell membrane or plasma membrane of a tumor cell. The TCAA is preferably, but not necessarily, tumor specific in that the antigen is restricted to or over-expressed by a tumor. Exemplary melanoma TCAAs include HLA Class I, Cd45, GD3, S100, HMB45, and MART-1. In the context of the present invention, a TCAA of a haptenized tumor cell vaccine can also be the cellular proteins decorated with hapten or haptens with which the tumor cells are associated or conjugated. Such hapten TCAAs include, without limitation, DNP, TNP, and SA. The density or level of a TCAA or TCAAs on a tumor cell, a level that is also termed "antigenicity" herein, can be measured using, e.g., FACS analysis with antibodies directed against the tumor-associated antigens.

The term "cell recovery" or "cell recovery rate" is a measure of how many cells are substantially intact, has a shape corresponding to or resembling that of a live cell, and/or has preserved antigenicity, after a certain period of storage or incubation. When calculating cell recovery, the number of cells at a certain time point or after a certain preparation step is related to the number of cells at a reference time point or prior to the preparation step in question.

The phrase "pharmaceutically acceptable" refers to molecular entities, at particular concentrations, and compositions that are physiologically tolerable and do not typically produce an allergic or similar untoward reaction, such as gastric upset, fever, dizziness and the like, when administered to a human or non-human animal. Preferably, as used herein, the term "pharmaceutically acceptable" means approved by a regulatory agency of the Federal or a state government, or listed in the U.S. Pharmacopoeia or other generally recognized pharmacopoeia for use in humans or non-human animals.

A "subject" is a human or a non-human animal who may receive haptenized tumor cells formulated in a composition of the invention. Non-human animals include domesticated pets, such as cats and dogs; farm animals, such as horses, cows, pigs, sheep, and goats; laboratory animals, such as mice, rats, guinea pigs, and rabbits; etc.

An "anti-tumor response" is at least one of the following: tumor necrosis, tumor regression, tumor inflammation, tumor infiltration by activated T lymphocytes, activation of tumor infiltrating lymphocytes, delayed-type hypersensitivity (DTH) response, or a clinical response. Clinical response criteria for anti-tumor response resulting from treatment according to the present invention include complete, partial, or mixed response, as well as stable disease. Other clinical responses that may be observed upon following the treatment of the invention is prolongation of time to relapse, or prolongation of survival.

A "formulation" refers to an aqueous medium or solution for the preservation or administration, or both, of haptenized tumor cells or tumor cell extracts, which is preferably directly injectable into an organism. The aqueous medium can include salts or sugars, or both, at about an isotonic concentration.

A "vaccine composition" is a composition as set forth previously further comprising an adjuvant, including an immunostimulatory cytokine or lymphokine.

The terms "vaccine", "immune therapy" and "immunotherapy" are used herein interchangeably to administration of a composition comprising a tumor cell preparation (preferably haptenized) to treat a cancer, e.g., after surgical resection of the tumor.

"Efficacy of an immunotherapy" is the degree to which the immunotherapy elicits an anti-tumor response in an individual subject, or the percentage of subjects in which an anti-tumor response develops as a result of treatment. Preferably efficacy is determined by composition to controls that harbor the spontaneous tumor but receive either no therapy, sham therapy, or an alternative therapy.

A "tumor cell preparation" refers to isolated or purified tumor cells or a tumor cell extract for inclusion in a composition. "Hapten modified" means that the tumor cells (or extract) are chemically coupled (conjugated) to a hapten, as that term is understood immunology.

The term "treat" means to attempt to elicit an antitumor response against cells of the tumor, i.e., the cancer. An antitumor response includes, but is not limited to, increased time of survival, inhibition of tumor metastasis, inhibition of tumor growth, tumor regression, and development of a delayed-type hypersensitivity (DTH) response to unmodified tumor cells.

As used herein, the term "control" generally describes a cell or cells not treated with freezing medium. The term control can also generally mean saline solution. More preferably, a control describes a composition which in essentially all other aspects other than freezing medium treatment has been exposed to the same conditions, and is stored in the same buffered medium and additional components.

Freezing Medium

As noted above, and demonstrated in the Examples, infra, it has been unexpectedly discovered that exposure of tumor cells to an appropriate freezing medium and then freezing the sample to the appropriate temperature, e.g., below 0° C., preferably from −80 to −196° C., maintains tumor cells, their antigenicity and their immunogenicity during cryopreservation. This is especially advantageous for tumor cells for use in immunotherapy vaccine preparations. The freezing medium of the present invention is a composition comprising an effective amount of sucrose and human serum albumin and an isotonic buffered saline solution to stabilize the haptenized tumor cells and preserve the antigenicity of the haptenized tumor cells during the freezing process. In a preferred embodiment, the freezing medium is composed of sucrose, human serum albumin and Hanks solution. Surprisingly, the use of sucrose and human serum albumin and an isotonic buffered saline solution in the freezing medium preserves the antigenicity, immunogenicity and stability during cryopreservation while maintaining the ability of the vaccine to be used in humans. Other components may be added to the freezing medium beyond sucrose, human serum albumin and Hank's solution, i.e., DMSO. However, a preferred embodiment of the freezing medium excludes DMSO.

In the present invention, the sucrose content may range from about 0.1% to about 40%. It is preferred that the sucrose content range from about 1% to about 20%. It is more preferred that the sucrose content range from about 5% to about 15%. A exemplified, preferred sucrose content is 8%. In addition to sucrose the freezing medium requires human serum albumin and an isotonic buffered saline solution. It is preferred that the human serum albumin content ranges from about 30% to about 1%. It is more preferred that the human serum albumin content range from about 5% to about 15%. It is still more preferred that the human serum albumin content is about 10%. Hanks buffered solution is a standard buffer solution and is discussed in more detail below. A preferred embodiment of the invention utilizes Hanks buffered solution in the freezing medium. It is contemplated that a skilled artisan will understand that other buffered salt solutions may be utilized, for example PBS. A very preferred embodiment of the freezing medium is a composition that is 8% sucrose, 10% human serum albumin in Hanks solution.

Depending on the specific tumor cells to be stored, and their modification, if any, one of ordinary skill in the art can optimize the freezing medium of the invention to their specific requirements. Such a freezing medium can be one that yields an increase in cell preservation relative to a control for stored tumor cells. For example, such a freezing medium can be one that retains the amount of antigen-expression and immunogenicity cells relative to a control. Preferably, the increase in preservation of the cells is statistically significant. In a very preferred embodiment, the cells are then stored at about −196° C. conditions. In one embodiment, the cells are first stored in a −80° C. freezer and then transferred to liquid nitrogen. By this method the preservation of antigen-expression and immunogenicity can be substantially preserved in haptenized tumor cell vaccine. Preferably, the preservation of a tumor cell subjected to freezing medium treatment and then frozen at −196° C. is greater than the same kind of tumor cells stored in control medium for the same period of time, at the same temperature.

The concentration of cells to be used during the freezing medium treatment step can be determined experimentally depending on the type of cells or cell preparation used. However, a generally suitable concentration is between $10^5$-$10^8$ cells, more preferably between $10^6$ to $10^7$ cells, and most preferably about $5 \times 10^6$ cells, per milliliter solution. The solution is advantageously, although not necessarily, isotonic.

Tumor cell extract such as membranes, tumor cell lysates where cell nuclei are removed, or simply lysed or disrupted cells, can be preserved according to similar procedures as described for intact, or substantially intact, tumor cells. Tumor cells or tumor cell extracts processed for use in an immunotherapy regimen as described below may be subjected to freezing medium treatment at any time during processing or formulation and cryopreserved. The concentration of cell membranes, lysed cells, or disrupted cells, is usually expressed as "cell equivalents", or "c.e.", herein.

For vaccines comprising haptenized tumor cells, freezing medium treatment and cryopreservation is preferably, although not necessarily, conducted after haptenization.

Tumor Cells

The tumor cells used in the present invention are prepared from tumor cells, e.g., obtained from tumors, or tissue or body fluids containing tumor cells, surgically resected or retrieved in the course of a treatment for a cancer. The sucrose freezing medium treated cryopreserved tumor cells are useful in the preparation of, e.g., tumor cell vaccines for treating cancer, including metastatic and primary cancers. If used in a tumor cell vaccine, the preserved tumor cells should be incapable of growing and dividing after administration into the subject, such that they are dead or substantially in a state of no growth. It is to be understood that "dead cells" means a cell which do not have an intact cell or plasma membrane and that will not divide in vivo; and that "cells in a state of no growth" means live cells that will not divide in vivo. Conventional methods of suspending cells in a state of no growth are known to skilled artisans and may be useful in the present invention. For example, cells may be irradiated prior to use such that they do not multiply. Tumor cells may be irradiated to receive a dose of 2500 cGy to prevent the cells from multiplying after administration. Alternatively, ethanol treatment may be used to create dead cells.

The tumor cells can be prepared from virtually any type of tumor. The present invention contemplates the use of tumor cells form solid tumors, including carcinomas; and non solid tumors, including hematologic malignancies. Examples of solid tumors from which tumor cells can be derived include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias, lymphomas, and multiple myelomas. The following are non limiting preferred examples of tumor cells to be preserved according to the present invention: melanoma, including stage-4 melanoma; ovarian, including advanced ovarian; small cell lung cancer; leukemia, including and not limited to acute myelogenous leukemia; colon, including colon metastasized to liver; rectal, colorectal, breast, lung, kidney, and prostate cancer cells.

Tumor cell vaccines can be prepared from any of the tumor cell types listed above. Such tumor cell vaccines can comprise preserved cells, i.e., cells treated with ethanol according to the method of the invention. Preferably, the vaccine comprises the same type of cells as the tumor to be treated. Most preferably, the tumor cells are autologous, derived from the patient for whom treatment with the vaccine is intended. Vaccines comprising tumor cells prepared using the method of the invention can used for treatment of both solid and non-solid tumors, as exemplified above. Thus, the invention includes "preserved" vaccines prepared from, and intended for treatment of, solid tumors, including carcinomas; and non solid tumors including hematologic malignancies. Preferred tumor types for vaccines include melanoma, ovarian cancer, colon cancer, and small cell lung cancer.

The tumor cells are preferably of the same type as, most preferably syngeneic (e.g., autologous or tissue-type matched) to, the cancer that is to be treated. For purposes of the present invention, syngeneic refers to tumor cells that are closely enough related genetically that the immune system of the intended recipient will recognize the cells as "self", e.g., the cells express the same or almost the same complement of HLA molecules. Another term for this is "tissue-type matched." For example, genetic identity may be determined with respect to antigens or immunological reactions, and any other methods known in the art. Preferably the cells originate from the type of cancer that is to be treated, and more preferably, from the same patient who is to be treated. The tumor cells can be, although not limited to, autologous cells dissociated from biopsy or surgical resection specimens, or from tissue culture of such cells. Nonetheless, allogeneic cells and stem cells are also within the scope of the present invention.

Tumor cells for use in the present invention may be prepared as follows. Tumors are processed as described by Berd et al. (Cancer Res. 1986; 46:2572; see also U.S. Pat. No. 5,290,551; U.S. patent application Ser. No. 08/203,004, Ser. No. 08/475,016, and Ser. No. 08/899,905). The cells are extracted by dissociation, such as by enzymatic dissociation with collagenase and DNase, or by mechanical dissociation such as with a blender, teasing with tweezers, mortar and pestle, cutting into small pieces using a scalpel blade, and the like. Mechanically dissociated cells can be further treated with enzymes as set forth above to prepare a single cell suspension.

Tumor cells may also be prepared according to Hanna et al., U.S. Pat. No. 5,484,596. Briefly, tumor tissue is obtained from patients suffering from the particular solid cancer from which the vaccine is to be prepared. The tumor tissue is surgically removed from the patient, separated from any non tumor tissue, and cut into small pieces, e.g., fragments 2-3 mm in diameter. The tumor fragments are then digested to free individual tumor cells by incubation in an enzyme solution. After digestion, the cells are pooled and counted, and cell viability is assessed. If desired, a trypan Blue exclusion test can be used to assess cell viability.

In addition, tumor cells can be prepared according to the following procedure (see Hanna et al., U.S. Pat. No. 5,484,596). The tissue dissociation procedure of Peters et al. (Cancer Research 1979; 39:1353 1360) can be employed using sterile techniques throughout under a laminar flow hood. Tumor tissue can be rinsed three times in the centrifuge tube with HBSS and gentamicin and transferred to a petri dish on ice. Scalpel dissection removed extraneous tissue and the tumor are minced into pieces approximately 2 to 3 mm in diameter. Tissue fragments are placed in a 75 ml flask with 20-40 ml of 0.14% (200 units/ml) Collagenase Type 1 (Sigma C-0130) and 0.1% (500 Kunitz units/ml) deoxyribonuclease type 1 (Sigma D-0876) (DNAase 1, Sigma D-0876) pre-warmed to 37° C. Flasks are placed in a 37° C. water bath with submersible magnetic stirrers at a speed that cause tumbling, but not foaming. After a 30-minute incubation, free cells are decanted through three layers of sterile medium wet nylon mesh (166t: Martin Supply Co., Baltimore, Md.) into a 50 ml centrifuge tube. The cells are centrifuged at 1200 rpm (250× g) in a refrigerated centrifuge for 10 minutes. The supernatant is poured off and the cells are resuspended in 5-10 ml of DNAase (0.1% in HBSS) and held at 37° C. for 5-10 minutes. The tube is filled with HBSS, washed by centrifugation, resuspended to 15 ml in HBSS and held on ice. The procedure is repeated until sufficient cells are obtained, usually three times for tumor cells. Cells from the different digests are then pooled, counted. Optionally, although not necessarily, cell viability is assessed by the Trypan Blue exclusion test.

The concentration of dissociated tumor cells can be adjusted to about $5-10 \times 10^7$/ml, or about $5 \times 10^7$ or $10 \times 10^7$ cells per ml, in sucrose freezing medium.

Tumor Cell Extracts

The tumor cells retrieved from tumors as described above may be further processed to yield tumor cell extracts for use in tumor cell vaccines.

To prepare tumor cell membranes for use in a vaccine, the following procedure can be used. Tumor cells are washed twice in Hanks balanced salt solution. Cells are suspended in about five volumes of about 30 mM sodium bicarbonate buffer with about 1 mM phenyl methyl sulfonyl fluoride and disrupted with a glass homogenizer. Residual intact cells and nuclei are removed by centrifugation at about 1000×g. The membranes are pelleted by centrifugation at 100,000 g for 90 minutes. The membranes are re-suspended in about 8% sucrose and frozen until needed, preferably, although not necessarily, at about −196° C. Other procedures for preparing tumor cell membranes are well known in the art as described in, e.g., WO 96/40173 and WO 99/40925, both by Berd et al. These publications also describe the extraction of tumor cell peptides, which also can be used in immunotherapy vaccines.

Alternatively, whole tumor cell extracts can be prepared simply by lysing cells using any of the methods known in the art, for example, homogenization or suspending the cells in a detergent or hypotonic solution, or cell lysis solution (e.g., Cytobuster™ from Novagen), containing additional components such as EDTA, protease inhibitors, and buffering components, as desired.

Haptens

In one embodiment, the tumor cells or tumor cell extracts are haptenized. For purposes of the present invention, virtually any small protein or other small molecule that fails to induce an immune response when administered alone, may function as a hapten. A variety of haptens of quite different chemical structure have been shown to induce similar types of immune response, e.g., TNP (Kempkes et al., J. Immunol., 1991; 147:2467); phosphorylcholine (Jang et al., Eur. J. Immunol., 1991; 21:1303); nickel (Pistoor et al., J. Invest. Dermatol., 1995; 105:92); and arsenate (Nalefski and Rao, J. Immunol., 150:3806, 1993). Conjugation of a hapten to a cell to elicit an immune response may preferably be accomplished by conjugation via ε-amino groups of lysine or —COOH groups. This group of haptens include a number of chemically diverse compounds: dinitrophenyl, trinitrophenyl, N-iodoacetyl-N'-(5-sulfonic 1-naphthyl) ethylene diamine, trinitrobenzene-sulfonic acid, dinitrobenzene sulfonic acid, fluorescein isothiocyanate, arsenic acid benzene isothiocyanate, and dinitrobenzene-S-mustard (Nahas and Leskowitz, Cellular Immunol., 1980; 54:241). Once armed with the present disclosure, skilled artisans would be able to choose haptens for use in the present invention.

Haptenization

A variety of haptens of different chemical structure have been shown to induce similar types of immune responses: e.g., dinitrophenyl (DNP); trinitrophenyl (TNP) (Kempkes et al., J. Immunol., 1991; 147:2467); phosphorylcholine (Jang et al., Eur. J. Immunol., 1991; 21:1303); nickel (Pistoor et al., J. Invest. Dermatol., 1995; 105:92); and arsenate (Nalefski and Rao, J. Immunol., 1993; 150:3806). Conjugation of a hapten to a cell can, for example, be accomplished by conjugation via ε-amino groups of lysine or —COOH groups. This group of haptens include a number of chemically diverse compounds: halonitrobenzenes (including dinitrofluorobenzene, difluorodinitrobenzene, trinitrofluoro-benzene), N iodoacetyl N' (5 sulfonic 1 naphthyl) ethylene diamine, nitrobenzene sulfonic acids (including trinitrobenzene-sulfonic acid and dinitrobenzene sulfonic acid), fluorescein isothiocyanate, arsenic acid benzene isothiocyanate, and dinitrobenezene S mustard (Nahas and Leskowitz, Cellular Immunol., 1980; 54:241).

In general, haptens include a "recognition group", which is the group that interacts with an antibody. The recognition group is irreversibly associated with the hapten reactive group. Thus, when the hapten reactive group is conjugated to a functional group on the target molecule, the hapten recognition group is available for binding with antibody. Examples of different hapten recognition groups include without limitation to dinitriophenyl, trinitrophenyl, fluorescein, other aromatics, phosphorylcholine, peptides, advanced glycosylation endproducts (AGE), carbohydrates, etc.

Haptens also include a functional group for conjugation to a substituent on an amino acid side chain of a protein or polypeptide. Amino acid side chain groups that can be conjugated to hapten include, e.g., free carboxylic acid groups in the aspartic aced or glutamic acid; the ε amino group of lysine; the thiol moiety of cysteine; the hydroxyl group of serine or tyrosine; the imidazole moiety of histidine; or the aryl groups of tryptophan, tyrosine, or phenylalanine. Hapten functional groups capable of reacting with specific amino acid side chains are described below.

Functional groups reactive with primary amines. Hapten reactive groups that would form a covalent bond with primary amines present on amino acid side chains would include, but not be limited to, acid chlorides, anhydrides, reactive esters, α,β-unsaturated ketones, imidoesters, and halonitrobenzenes. Various reactive esters with the capability of reacting with nucleophilic groups such as primary amines are available commercially, e.g., from Pierce (Rockford, Ill.).

Functional groups reactive with carboxylic acids. Carboxylic acids in the presence of carbodiimides, such as EDC, can be activated, allowing for interaction with various nucleophiles, including primary and secondary amines. Alkylation of carboxylic acids to form stable esters can be achieved by interaction with sulfur or nitrogen mustards, or haptens containing either an alkyl or aryl aziridine moiety.

Functional groups reactive with aromatic groups. Interaction of the aromatic moieties associated with certain amino acids can be accomplished by photoactivation of aryl diazonium compound in the presence of the protein or peptide. Thus, modification of the aryl side chains of histidine, tryptophan, tyrosine, and phenylalanine, particularly histidine and tryptophan, can be achieved by the use of such a reactive functionality.

Functional groups reactive with sulfhydryl groups. There are several reactive groups that can be coupled to sulfhydryl groups present on the side chains of amino acids. Haptens containing an α,β unsaturated ketone or ester moiety, such as maleimide, provide a reactive functionality that can interact with sulfhydryl as well as amino groups. In addition, a reactive disulfide group, such as 2-pyridyldithio group or a 5,5'-dithio-bis-(2-nitrobenzoic acid) group is also applicable. Some examples of reagents containing reactive disulfide bonds include N-succinimidly 3-(2-pyridyl-dithio) propionate (Carlsson, et al., Biochem J., 1978; 173:723-737), sodium S-4-succinimidyloxycarbonyl-alpha-methylbenzyl-thiosulfate, and 4 succinimidyloxycarbonyl-alpha-methyl-(2-pyridyldithio)-toluene. Some examples of reagents comprising reactive groups having a double bond that reacts with a thiol group include succinimidyl 4-(N-maleimidomethyl) cyclohexahe-1-carboxylate and succinimidyl m-maleimidobenzoate.

Other functional molecules include succinimidyl 3-(maleimido)-propionate, sulfosuccinimidyl 4-(p-maleimido-phenyl)butyrate, sulfo-succinimidyl 4-(N-maleimidomethyl-cyclohexane)-1-carboxylate, maleimidobenzolyl-N-hydroxysuccinimide ester. Many of the above-mentioned reagents and their sulfonate salts are available from Pierce (Rockford, Ill.).

Any hapten or combination of different haptens can be used in the compositions of the invention. For example in one embodiment, the same hapten recognition group is coupled to different amino acids through different functional groups. For example, the reagents dinitrobenzene sulfonic acid, dinitro phenyldiazonium, and dinitrobenzene S mustard, all form the dinitrophenyl hapten coupled to amino groups, aromatic groups, and carboxylic acid groups, respecively. Similarly, an arsonic acid hapten can be coupled by reacting arsonic acid benzene isothiocyanate to amino groups or azobenzenearsonate to aromatic groups. In another embodiment, the tumor cells are dual-haptenized, i.e., the same tumor cell preparation is conjugated with two different hatpens. The haptens may comprise reactive groups that react with different functional groups on the tumor cell, such as different amino acids. Such dual-haptenization is described in WO 00/38710 by Berd et al.

In yet another embodiment, the tumor cell can be bi-haptenized, i.e., two or more aliquots of a single tumor cell preparation is each coupled to a different hapten and mixed prior to administration or administered in conjunction with each other. Since, e.g., DNP modifies hydrophilic residues of MHC-bound peptides (mainly lysine $\epsilon$-amino groups) (Nahas and Leskowitz, Cellular Immunol, 1980; 54:241), the second hapten could advantageously be conjugated to hydrophobic residues (such as tyrosine and histidine). Such haptens, binding proteins through an azo linkage, include sulfanilic acid, arsanilic acid, and phosphorylcholine. Other haptens such as and not limited to trinitrophenyl, N-iodoacetyl-N'-(5-sulfonic 1-naphthyl) ethylene diamine, trinitrobenzene-sulfonic acid, fluorescein isothiocyanate, arsenic acid benzene isothiocyanate, trinitrobenzenesulfonic acid, sulfanilic acid, arsanilic acid, dinitrobenzene-S-mustard and combinations thereof may be similarly used.

Modification of the prepared cells with a hapten may be performed by known methods, e.g., by the method of Miller and Clanian (J. Immunol. 1976; 117:151). The described procedure involves a 30 minute incubation of tumor cells with DNFB under sterile conditions, followed by washing with sterile saline or Hanks/HSA. Other procedures for haptenization are known in the art (see. e.g., International Patent Publications WO 96/40173, WO 00/09140, WO 00/31542, WO 99/56773, WO 99/52546, WO 99/40925, WO 98/14206, WO 00/295, all by Berd et al., and U.S. Pat. No. 5,290,551 to Berd, hereby incorporated by reference in its entirety). The following procedures illustrate exemplary haptenization procedures.

DNP modification. Modification of the prepared cells with DNP or another hapten may be performed by known methods, e.g., by the method of Miller and Clanian (J. Immunol., 1976; 117:151), incorporated herein by reference in its entirety, which involves a 30 minute incubation of tumor cells with DNFB under sterile conditions, followed by washing with sterile saline or HBSS/HSA. For example about 100 mg of DNFB (Sigma Chemical Co., St. Louis, Mo.) can be dissolved in about 0.5 ml of 70% ethanol. About 99.5 ml of PBS is added. The solution is stirred overnight in a 37° C. water bath. The shelf life of the solution is about 4 weeks. The cells are thawed and the pellet resuspended in $5 \times 10^6$ cells/ml in Hanks balanced salt solution. About 0.1 ml DNFB solution is added to each ml of cells and incubated for about 30 minutes at room temperature.

SA modification. Modification of the prepared cells with SA may be performed by known methods. For example, in one embodiment, sulfanilic acid (SA) is converted to a diazonium salt by adding a saturating amount of sodium nitrite. Ice-cold, sterile filtered (0.2 µm), 10% sodium nitrite solution is added, dropwise, to a SA solution of 100 mg of anhydrous SA dissolved in 10 ml of 0.1N NCl until saturation. (The saturation point corresponds approximately to a final concentration of a sulfanilic acid diazonium salt of about 40 mM). The SA diazonium salt solution is then sterile filtered (0.2 µm membrane), and diluted 1:8 (v/v) in HBSS (without HSA). If needed, the pH is adjusted to 7.2 by dropwise addition of 1N NaOH. The SA diazonium salt/HBSS solution is then sterilized by filtration (0.2 µm membrane). Pelleted tumor cells are resuspended in diazonium salt/HBSS solution to a final concentration of $5 \times 10^6$ cells. The cell mixture is incubated for 5 minutes at room temperature. After the 5 minute incubation period, the hapenization reaction is stopped by the addition of 0.5 ml of a 25% HSA/HBSS solution to the cell mixture.

Formulations

The tumor cells and tumor cell extracts treated with freezing medium and cryopreserved according to the invention may be included in various formulations. For example, sucrose freezing medium treated, cryopreserved tumor cells may, in haptenized form, be useful for preparing tumor vaccines. The different components of such a formulation may be mixed together, and then added to tumor cells. It is also possible to mix one or several of the components with the tumor cells and then to add the remaining component(s). The preparation of the formulation and its addition of the tumor cells are preferably performed under sterile conditions. Preferably, the tumor cells are subjected to freezing medium treatment and cryopreservation before the final formulation. However, one or more components to be included in the final formulation may also be present before or during the sucrose freezing medium treatment and cryopreservation step.

Persons skilled in the art may adapt the respective proportions of the components of the medium according to the invention. As illustrated below, the proportions may be modified although certain concentration ranges are preferred.

Generally, an appropriate buffered medium is used for tumor cell formulation. In its essence, a buffered medium is an isotonic buffered aqueous solution, such as phosphate buffered saline (PBS), Tris-buffered saline, or HEPES buffered saline. In a preferred embodiment, the medium is a buffered cell culture medium such as plain Hank's medium (not containing phenol red), e.g., as sold commercially by Sigma Chemical Co. (St. Louis, Mo., USA). Other tissue culture medium can also be used, including basal medium Eagle (with either Earle's or Hank's salts). Dulbecco's modified, Eagle's medium (DMEM), Iscove's modified Dulbecco's medium (IMDM), Medium 199, Minimal Essential Medium (MEM) Eagle (with Earle's or Hank's salts), RPMI, Dulbecco's phosphate buffered salts, Earle's balanced salts (EBSS), and Hank's Balanced Salts (HBSS). These mediums can be supplemented, e.g., with glucose, Ham's nutrients, or HEPES. Other components, such as sodium bicarbonate and L-glutamine, can be specifically included or omitted. Medium, salts, and other reagents can be purchased from numerous sources, including Sigma, Gibco, BRL, Mediatech, and other companies.

Generally, human serum albumin (HSA) is also included, as described below. In addition, a composition or formulation of the invention may contain components in addition to HSA to further stabilize the haptenized tumor cells. Examples of such components include, but are not limited to, carbohydrates and sugars such as sucrose, glucose, and the like, e.g., at a 5% concentration; medium to long chain polyols such as glycerol, polyethylene glycol, and the like, e.g., at 10% concentration; other proteins; amino acids; nucleic acids; chelators; proteolysis inhibitors; preservatives; and other components. Preferably, any such constituent of a composition of the invention is pharmaceutically acceptable.

Human Serum Albumin

In a preferred embodiment, the tumor cell formulations of the invention comprise a concentration or amount of a protein such as, e.g., albumin, which is effective to stabilize the tumor cells. An amount of protein effective to stabilize the tumor cells may be added before and/or after cryopreservation, or, in the case of haptenized tumor cells, before and/or after haptenization. In a preferred embodiment, the albumin is human serum albumin or HSA. HSA has been shown to stabilize solutions of proteins, including protein antigens, and small organic molecules such as hemin (Paige, A. G. et al., Pharmaceutical Res., 12:1883-1888, 1995; Chang, A. C. and R. K. Gupta, J., Pharm. Sci., 85:129-132, 1996; Niemeijer, N. R. et al., Ann. Allergy Asthma Immunol., 76:535-540, 1996; and Cannon, J. B. et al., PDA:J. Pharm. Sci. & Tech., 49:77-82, 1995), as well as haptenized tumor cell compositions (see WO 00/29554, corresponding to U.S. Pat. No. 6,248,585).

The HSA used within the framework of the present invention may be either of natural origin (purified HSA) or of recombinant origin (rHSA). Naturally, for delivery of a formulation in vivo, it is preferably to use an autologous or non-immunogenic serum albumin. Thus, for human therapy, HSA is desirable and preferred. However, the skilled person can immediately appreciate that any serum albumin can be used in the practice of this invention, and, more particularly, any autologous serum albumin can be used in connection with tumor cell vaccine for cancer treatment in any non-human animal as well. In a specific embodiment, a Human Serum Albumin Solution (American Red Cross), which is a 25% HSA solution, is used.

Advantageously, a recombinant or natural HSA is used which meets certain quality criteria (e.g., homogenetic, purity, stability). Thus, the pharmacopoeias set a number of parameters for the albumin solutions, namely a pH value, a protein content, a polymer and aggregate content, an alkaline phosphatase content, and a certain protein composition. It imposes, furthermore, a certain absorbance, the compliance with tests for sterility, pyrogens, and toxicity (see "Albumini humai solution", European Pharmacocpoeia (1984), 255). The use of an albumin composition corresponding to these criteria, although not essential, is particularly preferred.

Generally, the HSA formulation of the invention is made by adding HSA powder or solution to the selected culture medium/balanced salt solution, to achieve the desired final concentration, as set forth above.

Additional information about the use of albumin in formulations of tumor cells, especially haptenized tumor cells, can be found in WO 00/29554, corresponding to U.S. Pat. No. 6,248,585.

Vaccine Preparation and Administration

The compositions of the invention may be administered in a mixture with a pharmaceutically acceptable carrier, selected with regard to the intended route of administration and standard pharmaceutical practice. Dosages may be set with regard to weight and clinical condition of the patient. The proportional ratio of active ingredient to carrier naturally depends on the chemical nature, solubility, and stability of the compositions, as well as the dosage contemplated. The amounts to be used of the tumor cells of the invention depend on such factors as the affinity of the compound for cancerous cells, the amount of cancerous cells present and the solubility of the composition. Any suitable route, including inoculation and injection modes using, for example, intradermal, intravenous, intraperitoneal, intramuscular, and subcutaneous routes, may administer the compounds of the present invention. For example, the composition may be administered by intradermal injection into 3 contiguous sites per administration on the upper arms or legs, excluding limbs ipsilateral to a lymph node dissection. In addition, the vaccine may be given by subcutaneous injection close to the site of a tumor excision.

Tumor Cell Dose

Traditionally, the amount of tumor cells to be included in tumor cell vaccines has been determined based upon the number of viable, i.e., Trypan Blue-excluding, cells (see, e.g., Hoover et al., 1985; 55:1236-1243; and U.S. Pat. No. 5,484, 596 to Hanna et al.). According to a preferred embodiment of the invention, the number of tumor cells in the tumor cell vaccine to be administered to the patient is not based upon the number of viable tumor cells, but on the total number of tumor cells, i.e., both live and "dead" cells as assessed by Trypan Blue exclusion.

The total cell counting procedure can be carried out by any suitable method known in the art. For example, cells can be counted manually using a microscope and standard cell counting chambers, or by using automatic cell counters such as, e.g., Beckman Coulter cell counters. Since the method does not require distinguishing between live and "dead" cells, Trypan Blue and other means, which are selective for live or dead cells, can be omitted. The concentration of cells can then be adjusted by diluting the cells with a sterile solution so that a certain volume corresponds to the number of cells to be injected into the patient, and this volume aliquoted into storage vials.

In a preferred embodiment of the invention, the composition comprises a vaccine comprising about $1\times10^4$ to $1\times10^8$, more preferably $1\times10^6$ to about $25\times10^6$, even more preferably about $2.5\times10^6$ to about $7.5\times10^6$, tumor cells or tumor cell equivalents suspended in a pharmaceutically acceptable carrier or diluent, such as, but not limited to, Hank's solution (HBSS), saline, phosphate buffered saline, and water.

Adjuvants

In preferred embodiment, a tumor cell composition may be administered with an immunological adjuvant. While the commercial availability of pharmaceutically acceptable adjuvants is limited, representative examples of adjuvants include Bacille Calmette-Guerin, BCG, or the synthetic adjuvant, QS-21 comprising a homogeneous saponin purified from the bark of Quillaja saponaria, Corynebacterium parvum, (McCune et al., Cancer 1979; 43:1619), and IL-12.

It will be understood that the adjuvant is subject to optimization. In other words, the skilled artisan can engage in no more than routine experimentation and determine the best adjuvant to use.

Immunostimulants and Combination Therapies

The tumor cell compositions may be co-administered with other compounds including but not limited to cytokines such as interleukin-2, interleukin-4, gamma interferon, interleukin-12, GM-CSF. The tumor cells and extracts of the invention may also be used in conjunction with other cancer treatments including but not limited to chemotherapy, radiation, antibodies, antisense oligonucleotides, and gene therapy.

EXAMPLES

Example 1

Frozen Vaccine Processing

This Example describes the processing and storage of tumor cells. The tumor cells are prepared from patient tumors, haptenized, and frozen.

Materials and Equipment

Collagenase (Sigma cat.#C1639 or C9722); Hanks Balanced Salt Solution without phenol red (Gibco/BRL cat. #14175-095 or equivalent); EDTA disodium (IBI cat.#IB70182, Sigma #E8008 or equivalent); sucrose certified A.C.S. (Fisher Cat.#S5 3 or equivalent); PBS (calcium, magnesium, free) (Sigma Cat.# D8537 or equivalent); DNFB (Sigma Cat. #D1529); Nalgene filter units (PES) 0.20 μm (Cat.#165-0020) or equivalent; Falcon 50 ml and 15 ml centrifuge tubes or equivalent; Trypan Blue 0.4% (Gibco/BRL Cat.#15-250-061 or equivalent); isopropanol; cryovials, 1.0 ml., externally threaded (VWR Cat. #66021-994, or Fisher Cat #12-565-164N); #50 Mesh Screen; human albumin (HSA) 25%; Class II Biological Safety Cabinet; Nalgene Cryo Container Cat. #5100-0001; hemacytometer; microscope.

Procedure

Although tumor cells from any solid tumor can be prepared using the following procedure, the procedure is particularly suitable for melanoma and ovarian carcinoma. A dissected tumor is transferred to a biosafety cabinet and tested for sterility. The tumor is removed from the transport medium with sterile forceps and submerged successively for 1 minute each in three specimen containers with 50 ml of sterile Hanks solution. The tumor is then transferred to a Petri dish for weighing.

Five to 10 ml of Hanks solution is added, and tumors are cut with a scalpel into pieces of approximately 3 mm or less in diameter. The solution is removed with a pipette, and the tumor pieces are transferred to a sterile, disposable baffled flask and a sterile magnetic stir bar is added. Tumors are digested with 50 ml wash and thaw (500 ml Hanks buffer+0.5 g EDTA+2 ml 25% HSA, adjusted to pH to 7.2 by addition of 1N NaOH) containing 70 mg collagenase. Collagenase solutions are filtered through 0.2 mm filters prior to use. Digestion is allowed to proceed for 30 min at 37° C. with stirring. After digestion, the tumor is filtered through a wire mesh screen and the flow through containing the cells is collected.

Cells are pelleted by centrifuging for 7 minutes at 276×g at room temperature and re-suspended in 20 ml Hanks solution without HSA. Cells are pelleted by centrifuging for 7 minutes at 276×g at room temperature and re-suspended in 10 ml Hanks solution without HSA. A 10 ml aliquot is removed aseptically and diluted in 0.2% Trypan blue (25 ml 0.4% Trypan blue stock+25 ml PBS Ca/Mg free). Cells are enumerated in a hemacytometer and the numbers of trypan blue excluding tumor cells (I), trypan blue staining tumor cells (NI) and lymphocytes (L) will be recorded (after digestion and cell count). Optionally, the cells can be irradiated. The cells may also be haptenized, as described below, by adding DNFB stock solution and incubating the cells for 30 min at room temperature with mixing every 10 minutes by inversion of the tubes.

Cells are thereafter pelleted by centrifuging for 7 minutes at 276×g at room temperature. All the supernatant (10 mL) is transferred and placed in a sterile, labeled tube at 4° C. This sample is tested for sterility. The cells are re-suspended in 2 ml sterile freezing medium (60 ml Hanks solution+8 g sucrose+40 ml 25% HSA, adjusted to pH 7.2; filter through a 0.2 mm filter). In cases where there are a very large number of cells, re-suspended in the minimum volume possible. Preferably, the final concentration of cells is about $25 \times 10^6$ cells/mL. The cell vials are placed into a Nalgene Cryo 1° C. Container containing isopropanol and placed in the −80° C. freezer overnight. The next day, the vials are transferred to liquid nitrogen for storage.

Example 2

Distribution of Cell Types After Digestion, Haptenization and Freezing and Thawing Melanoma vaccines are relatively uniform with respect to cellular composition, i.e., proportion of intact cells, non-intact cells and lymphocytes, despite the natural variability of the starting tumors. Freezing and thawing of the vaccine results in significant conversion of intact cells to non-intact cells. However, irradiation during the preparation of the vaccine does not affect the cellular composition of melanoma vaccines.

The cellular compositions of melanoma vaccines at three stages of manufacture, after digestion, after haptenization, and after freezing and thawing, are presented in Table 1. As expected because each tumor is a unique entity, there was considerable variability among the individual tumors at the first point at which a count was done, i.e., post-digestion. However, for a given vaccine, the proportion of each cell type changed little as a result of haptenization, but significant changes were observed following freezing and thawing.

TABLE 1

| | Cell Type (%)[1] | | | | | | | | |
|---|---|---|---|---|---|---|---|---|---|
| | I | | | NI | | | L | | |
| Vaccine | After Digest | After Hapten | After Thaw | After Digest | After Hapten | After Thaw | After Digest | After Hapten | After Thaw |
| Non-Irradiated | | | | | | | | | |
| LTB | 12.2 | 6.1 | 1.8 | 41.8 | 74.0 | 86.3 | 46.0 | 19.9 | 11.9 |
| ES | 20.5 | 16.7 | 2.3 | 31.8 | 16.2 | 90.1 | 47.7 | 67.2 | 7.7 |
| VD | 5.1 | 3.7 | 8.2 | 46.1 | 29.9 | 77.4 | 48.8 | 66.4 | 14.4 |
| PAG | 50.7 | 39.2 | 4.2 | 14.5 | 19.1 | 79.2 | 34.8 | 41.7 | 16.6 |
| RLT | 6.7 | 2.0 | 7.7 | 47.1 | 12.1 | 77.6 | 46.2 | 85.9 | 14.7 |
| PSB | 2.2 | 3.8 | 1.1 | 79.8 | 78.7 | 69.0 | 18.0 | 17.5 | 29.9 |

TABLE 1-continued

| | Cell Type (%)[1] | | | | | | | | |
|---|---|---|---|---|---|---|---|---|---|
| | I | | | NI | | | L | | |
| Vaccine | After Digest | After Hapten | After Thaw | After Digest | After Hapten | After Thaw | After Digest | After Hapten | After Thaw |
| MD | 10.3 | 11.6 | 1.2 | 67.3 | 39.5 | 88.1 | 224 | 48.8 | 10.7 |
| RM | 28.6 | 38.3 | 20.0 | 46.4 | 41.3 | 70.6 | 25.0 | 20.3 | 9.4 |
| EM | 12.9[1] | 13.6 | 2.2 | 70.0[1] | 74.6 | 86.0 | 17.1[1] | 11.9 | 11.8 |
| DUI | 7.3 | 7.2 | 3.2 | 69.9 | 71.7 | 80.5 | 22.8 | 21.1 | 16.3 |
| TB | 41.2 | 53.1 | 2.8 | 27.5 | 26.5 | 85.5 | 31.4 | 20.4 | 11.7 |
| TWL | NT | NT | NT | NT | NT | NT | NT | NT | NT |
| Mean | | | | | | | | | |
| Std Dev | | | | | | | | | |
| | | | | Irradiated | | | | | |
| JHW | 16.2 | 15.7 | 1.3 | 19.1 | 12.7 | 79.2 | 64.7 | 71.6 | 19.5 |
| JD2 | 32.0 | 27.0 | 4.1 | 51.5 | 30.1 | 82.1 | 16.6 | 42.9 | 13.9 |
| VFE | 38.5 | 43.6 | 10.9 | 21.4 | 20.1 | 80.5 | 40.1 | 36.2 | 8.7 |
| CP | 10.7 | 17.3 | 0 | 33.1 | 40.0 | 77.9 | 56.2 | 42.7 | 22.1 |
| LD | 16.2 | 14.8 | 3.8 | 54.5 | 48.1 | 79.2 | 29.2 | 37.0 | 17.0 |
| Mean | 22.7 | 23.7 | 4.0 | 35.9 | 30.2 | 79.8 | 41.4 | 46.1 | 16.2 |
| Std Dev | 11.9 | 12.2 | 4.2 | 16.5 | 14.4 | 1.6 | 19.6 | 14.6 | 5.2 |
| | | | | Non-Irradiated | | | | | |
| Mean | 18.8 | 19.6 | 4.7 | 45.0 | 39.7 | 80.6 | 33.9 | 40.7 | 14.8 |
| Std Dev | 14.5 | 15.9 | 5.0 | 19.8 | 25.0 | 5.8 | 15.0 | 22.3 | 5.6 |

NT = Not Tested; NA = Not Applicable
[1] I = Intact Cells (trypan blue excluding), NI = Non-Intact Cells (trypan blue positive), L = Lymphocytes
2 Digestion solution included gentamycin
3 TCE vaccine passed test; TCM vaccine failed test Results: The small change in the proportion of each cell type as a result of haptenization is reflected in the similar results post-digestion and post-haptenization, both for individual vaccines and for the means. The significant changes as a result of freezing and then thawing of the vaccine are reflected in the observed decreases of intact tumor cells (I) with concomitant increases in the amount of non-intact (NI) tumor cells as well as decreases in the proportion of lymphocytes. This change was observed in all cases except those vaccines for which a low percent of intact tumor was observed initially (patients VD, RLT and PSB).

Overall, the variability in the proportions of different cell types among the post-thaw samples of the vaccines was much less than for post-digestion and post-haptenization samples, as reflected in the much smaller standard deviation, demonstrating that the vaccines were relatively uniform despite the variability of the starting tumors. Further, there was no obvious difference between those vaccines that were irradiated during preparation versus those that were not. The mean proportions of the different cell types in the various fractions was very similar for irradiated samples alone compared to the mean proportions for all samples, irradiated or not.

Example 3

Retention of HLA Class I Antigen and Surface DNP After Sucrose-Freezing Medium Treatment and Cryopreservation This Example describes the cell recovery and antigenicity of haptenized cells when treated with freezing medium, comprised of sucrose, human serum albumin and Hank's buffered solution and stored in liquid nitrogen for up to 7 months. Both irradiated and non-irradiated vaccine samples were tested. Cell counting and flow cytometry were conducted as described below.

As shown in the table below, sucrose freezing medium treatment followed by cryopreservation resulted in little evidence of a significant diminution of surface DNP or surface HLA class I antigen.

TABLE 2

Stability of Surface DNP and HLA Class I of Melanoma Vaccine Stored in Liquid Nitrogen for up to 7 Months

| | | Shift (%) | | | | | |
|---|---|---|---|---|---|---|---|
| | | Surface DNP | | | HLA Class I | | |
| Vaccine | Time Point (mo) | Total Shift (Anti-DNP) | Background (Isotype) | DNP-Isotype | Total Shift (HLA Class I) | Background (Isotype) | HLA Class I-Isotype |
| | | Non-Irradiated | | | | | |
| LTB | 0 | 82.35 | 24.00 | 58.35 | 71.99 | 24.00 | 47.99 |
| | 3.5 | 91.45 | 24.15 | 67.30 | 73.67 | 24.15 | 49.52 |
| | 7 | 86.15 | 25.14 | 61.01 | 66.01 | 25.14 | 40.87 |

TABLE 2-continued

Stability of Surface DNP and HLA Class I of Melanoma
Vaccine Stored in Liquid Nitrogen for up to 7 Months

| | | Shift (%) | | | | | |
|---|---|---|---|---|---|---|---|
| | | Surface DNP | | | HLA Class I | | |
| Vaccine | Time Point (mo) | Total Shift (Anti-DNP) | Back-ground (Isotype) | DNP-Isotype | Total Shift (HLA Class I) | Back-ground (Isotype) | HLA Class I-Isotype |
| BS | 0 | 63.48 | 23.24 | 40.24 | 98.02 | 19.48 | 78.54 |
| VD | 0.5 | 85.65 | 26.90 | 58.75 | 98.60 | 26.90 | 71.70 |
| | 3 | 36.36 | 19.89 | 16.47 | 96.20 | 19.89 | 76.31 |
| | 5.2 | 40.29 | 24.10 | 16.19 | 94.14 | 24.10 | 70.04 |
| PAG | 3 | 88.58 | 14.78 | 73.80 | 89.18 | 14.78 | 74.40 |
| | 5.2 | 87.69 | 12.12 | 75.57 | 88.39 | 12.12 | 76.27 |
| RLT | 0 | 89.80 | 14.75 | 75.05 | 90.70 | 14.75 | 75.95 |
| | 3 | 86.50 | 29.14 | 57.36 | 86.77 | 29.14 | 57.63 |
| | 6 | 86.84 | 13.46 | 73.4 | 94.89 | 13.46 | 81.43 |
| PSB | 0 | 97.62 | 38.47 | 59.15 | 96.27 | 38.47 | 57.80 |
| | 3 | 85.33 | 28.05 | 57.28 | 88.90 | 28.05 | 60.85 |
| MD | 0 | 96.62 | 35.54 | 61.08 | 98.26 | 35.54 | 62.72 |
| | 4 | 92.84 | 23.64 | 69.20 | 91.49 | 23.64 | 67.85 |
| RM | 0 | 66.32 | 27.50 | 38.82 | 97.28 | 27.50 | 69.78 |
| DUI | 0 | 80.82 | 21.53 | 59.29 | 72.29 | 21.53 | 50.76 |
| | 2 | 64.37 | 24.14 | 40.23 | 63.37 | 24.14 | 56.99 |
| | 3 | 85.42 | 27.71 | 58.25 | 79.67 | 27.71 | 51.96 |
| TB | 0 | 82.73 | 12.30 | 70.43 | 83.71 | 12.30 | 71.41 |
| | 1 | 86.22 | 24.67 | 61.55 | 91.24 | 24.67 | 66.57 |
| | 3.5 | 94.55 | 26.48 | 68.07 | 92.56 | 26.48 | 66.08 |
| | | Irradiated | | | | | |
| JD2 | 0 | 79.03 | 14.53 | 64.50 | 52.30 | 14.53 | 37.77 |
| | 1 | 92.63 | 30.82 | 61.81 | 65.28 | 10.82 | 34.46 |
| | 3.5 | 97.84 | 20.09 | 77.75 | 66.04 | 20.09 | 45.95 |
| VFE | 0 | 67.72 | 11.79 | 55.93 | 98.09 | 11.79 | 86.30 |
| | 2 | 89.60 | 19.03 | 70.57 | 98.94 | 19.03 | 79.91 |
| | 3 | 89.84 | 18.51 | 71.33 | 98.90 | 18.51 | 80.39 |
| CP | 0 | 51.53 | 27.37 | 24.16 | 98.94 | 27.37 | 71.57 |
| | 1 | 81.34 | 18.10 | 63.33 | 96.47 | 18.10 | 78.37 |
| | 2.5 | 26.09 | 28.35 | 0.00 | 99.48 | 28.35 | 71.13 |
| LD | 0 | 76.95 | 26.01 | 50.94 | 85.04 | 26.01 | 59.03 |
| | 2 | 78.75 | 24.24 | 54.51 | 77.70 | 24.24 | 53.46 |
| | 3 | 79.67 | 26.05 | 53.62 | 79.93 | 26.05 | 53.88 |
| | | Irradiated | | | | | |
| LC | 0 | 87.06 | 18.86 | 68.20 | 54.46 | 18.86 | 35.60 |
| | 2 | 95.54 | 20.23 | 75.31 | 53.55 | 20.23 | 33.32 |
| JHW [1] | 0 | 44.91 | 22.45 | 22.46 | 97.50 | 22.45 | 75.05 |
| | 1.5 | 59.86 | 48.79 | 11.07 | 98.90 | 48.79 | 50.11 |
| | 2 | 44.61 | 21.22 | 23.39 | 98.16 | 21.22 | 76.94 |
| | 4 | 48.64 | 21.49 | 27.15 | 97.99 | 21.49 | 76.50 |

[1] Due to calculation error, received only half the amount of DNFB

Protocol: The irradiated and non-irradiated haptenized cells were contacted with freezing medium. The freezing medium was comprised of 8% sucrose, 10% human serum albumin and Hank's buffered solution. The samples were frozen overnight in a −80° C. freezer and then transferred to a liquid nitrogen freezer for storage.

Results: The results for both the irradiated and non-irradiated haptenized tumor cells shows that the surface hapten DNP or surface HLA class I antigen was maintained over several months of storage. Only one sample, designated VD in Table 2, showed any consistent loss of haptenization and freezing medium treatment and long-term storage in liquid nitrogen.

Cytometry Procedures

The tumors samples were removed from liquid nitrogen, placed at −196° C. overnight and then thawed in a 37° C. water bath for approximately 90 sec and placed on ice. The samples may be filtered at this time using a 70 μm Falcon nylon filter. The samples were split into 7 tubes, 3 tubes for surface staining and 4 tubes for internal staining. The surface samples were washed in 1 ml/tube of wash buffer (phosphate-buffered saline with 0.1% bovine serum albumin and 0.1% NaN3) and cells were pelleted at 1500 rpm for 7 minutes at 4° C. All but 100 μl of the wash was discarded and 1.1 μg of either mouse anti-human HLA-ABC (Dako cat #M0736; IgG2a); mouse anti-DNP (Sigma cat #8406), or a mouse IgG2a control isotype control antibody was added to the samples. After incubation for 1 hr at 4° C., the cells were washed in 3 ml of wash buffer and pelleted at 1500 rpm for 7 minutes at 4° C. All but 100 μl of the wash was aspirated and 5 μl of secondary antibody, rabbit anti-mouse Ig conjugated with fluorescein isothiocyanate (FITC, Dako cat #F0313) was added to each sample tube. After incubation for 45-60 min at 4° C., the samples were washed one more time with 3 ml of wash buffer and cells were pelleted at 1500 rpm for 7 minutes at 4° C. After the last wash, all but 100 μl of the wash was aspirated from the tubes and cells were re-suspended in 2 ml of wash buffer. Samples were read on a Beckman Coulter Epics Altra flow cytometer and the data was analyzed using Expo 32® software (Applied Cytometry Systems). The shift was determined by calculating the percentage of events that had a fluorescence greater than that at the half-maximum peak height on the right-hand side of the curve for the isotype control antibody, as described by Erdile et al., (J. Immunol. Meth., 2001; 258:47-53).

Example 4

Stability of Sucrose Freezing Medium-Treated Cryopreserved Cells

This Example compares long-term stability of irradiated and non-irradiated DNP-haptenized melanoma cells. Briefly, cells were suspended in freezing medium comprising 8% sucrose 10% human serum albumin and Hank's buffered solution, placed in a −80° C. freezer overnight, and transferred to a liquid nitrogen freezer for storage. At various time points up to 9 months, samples were thawed and the relative fractions of intact cells, non-intact cells, and lymphocytes were determined. The results are shown in Table 3.

The percentages of the different cell types remained relatively unchanged over at least the first 3 months of storage, and the variation between irradiated and non-irradiated tumor cell samples was small. The results show that the freezing medium preserves haptenized tumor cells.

TABLE 3

Stability of Cellular Composition of Melanoma Vaccine Stored in Liquid Nitrogen Up to 9 Months

| Vaccine | Time (Months) | Cell Type (%)[1] | | |
|---|---|---|---|---|
| | | I | NI | L |
| Non-Irradiated | | | | |
| LTB | 0 | 1.8 | 86.3 | 11.9 |
| | 0.5 | 2.6 | 80.9 | 16.5 |
| | 1 | 2.5 | 83.0 | 14.5 |
| | 2 | 2.3 | 84.7 | 13.0 |
| | 3 | 3.9 | 94.4 | 1.7 |
| | 7 | 2.9 | 89.7 | 7.4 |
| | 9 | 1.9 | 93.3 | 4.8 |
| VD | 0 | 8.2 | 77.4 | 14.4 |
| | 0.5 | 8.0 | 59.4 | 32.6 |
| | 1 | 4.2 | 79.0 | 16.8 |
| | 2 | 3.2 | 84.2 | 12.6 |
| | 3 | 0.5 | 81.4 | 18.0 |
| | 5.5 | 0.8 | 78.4 | 20.8 |
| PAG | 0 | 4.2 | 79.2 | 16.6 |
| | 0.5 | 4.0 | 87.0 | 9.1 |
| | 1 | 5.2 | 45.0 | 49.8 |
| | 2 | 7.5 | 86.3 | 6.2 |
| | 3 | 2.9 | 78.6 | 18.4 |
| RLT | 0 | 7.7 | 77.6 | 14.7 |
| | 0.5 | 6.0 | 88.0 | 6.0 |
| | 1 | 12.0 | 83.7 | 4.2 |
| | 2 | 5.5 | 75.2 | 19.3 |
| | 3 | 5.0 | 69.5 | 25.5 |
| | 5.5 | 6.5 | 79.7 | 13.8 |
| PSB | 0 | 1.1 | 69.0 | 29.9 |
| | 0.5 | 3.7 | 46.3 | 50.0 |
| | 1 | 0.5 | 87.5 | 12.0 |
| | 2 | 1.8 | 79.0 | 19.2 |
| | 3 | 3.0 | 74.7 | 22.3 |
| | 6 | 0/0 | 87.5 | 12.5 |
| MD | 0 | 1.2 | 88.1 | 10.7 |
| | 0.5 | 0.5 | 49.5 | 50.0 |
| | 1 | 0.0 | 88.7 | 11.3 |
| | 2 | 1.4 | 61.4 | 37.2 |
| | 3 | 0.0 | 66.7 | 33.3 |
| | 4 | 1.2 | 85.5 | 13.3 |
| | 5.5 | 0.0 | 93.1 | 6.9 |
| DUI | 0 | 3.2 | 80.5 | 16.3 |
| | 0.5 | 0.0 | 87.4 | 12.6 |
| | 1 | 0.0 | 91.7 | 8.3 |
| | 2 | 2.3 | 91.9 | 5.8 |
| | 3 | 4.9 | 76.9 | 18.2 |
| TB | 0 | 2.8 | 85.5 | 11.7 |
| | 0.5 | 5.1 | 78.1 | 17.7 |
| | 1 | 1.9 | 75.8 | 22.8 |
| | 2 | 2.0 | 82.0 | 16.4 |
| | 3.5 | 0.7 | 88.1 | 11.2 |
| Irradiated | | | | |
| JHW | 0 | 1.3 | 79.3 | 19.5 |
| | 1 | 5.2 | 86.7 | 8.6 |
| | 1.5 | 0.0 | 80.2 | 19.8 |
| | 2 | 5.1 | 68.5 | 27.8 |
| | 4 | 1.1 | 93.0 | 5.9 |
| JD2 | 0 | 4.1 | 82.1 | 13.9 |
| | 0.5 | 2.2 | 86.7 | 11.4 |
| | 1 | 0.0 | 85.0 | 15.0 |
| | 2 | 5.3 | 75.8 | 19.9 |
| | 3.5 | 5.4 | 74.5 | 21.3 |
| VFE | 0 | 10.9 | 80.5 | 8.7 |
| | 1 | 6.2 | 69.2 | 26.2 |
| | 2 | 3.0 | 86.5 | 10.8 |
| | 3 | 4.1 | 84.0 | 12.4 |
| CP | 0 | 0.0 | 77.9 | 22.1 |
| | 0.5 | 0.8 | 76.8 | 22.6 |
| | 1 | 0.0 | 83.2 | 16.8 |
| | 2 | 0.0 | 90.8 | 9.2 |
| | 2.5 | 0.0 | 92.2 | 7.8 |
| LD | 0 | 3.8 | 79.2 | 17.0 |
| | 1 | 10.0 | 75.0 | 16.7 |
| | 2 | 10.4 | 85.7 | 4.3 |
| | 3 | 0.0 | 87.1 | 12.9 |
| LC | 0 | 2.9 | 81.2 | 15.9 |
| | 1 | 4.9 | 81.7 | 14.1 |
| | 2 | 1.8 | 93.0 | 5.3 |

[1]I= Intact Cells (trypan blue excluding), NI = Non-Intact Cells (trypan blue positive), L = Lymphocytes Example 5

In Vivo Efficacy of Cryopreserved Vaccine

This Example describes the evaluation of the therapeutic efficacy of frozen dinitrophenyl (DNP)-modified tumor cell vaccine against tumor recurrence in mice from which a primary 410.4 mammary carcinoma was surgically excised. The results show that frozen DNP-modified tumor cell vaccine is equally effective in improving relapse-free survival as a fresh DNP-modified tumor cell vaccine (Sojka et al., Cancer Immunol. Immunother, 2002; 51:200-208). The improvement in relapse-free survival was consistent between 4 independent experiments, and, when the data from all 4 studies were pooled, the effect was statistically significant. A direct comparison of frozen and fresh DNP-modified tumor cell vaccine suggested their efficacy was indistinguishable. Further, the relapse-free survival of mice immunized with frozen DNP-modified tumor cell vaccine was also superior to that of mice immunized with frozen unmodified tumor cell vaccine in 3 independent experiments, and the difference was statistically significant when the data from all 3 studies were pooled. Accordingly, DNP-modification improves the therapeutic benefits of this tumor cell vaccine, and the cryopreservation method employed does not diminish the vaccine potency. Preliminary results also indicated that subjecting the tumor cells to gamma irradiation prior to their DNP modification improved vaccine efficacy. The vaccine was well-tolerated, showing only mild, self-limited induration at the injection site. The materials and experimental design, as well as the results, are discussed in more detail below.

The animal model employed the highly metastatic 410.4 tumor that originates from a spontaneously arising BALB/c murine mammary carcinoma. Tumor cells were maintained in vitro as previously described (Sojka et al., Cancer Immunol. Immunother. 2002; 51:200-208), and $3\times10^5$ tumor cells were injected into mammary fatpads of the left breast of female BALB/cAnNCrBR mice 7-10 weeks old (Charles River Breeding Laboratories, Wilmington, Mass.). Tumors were allowed to grow to 6-8 mm in diameter, at which point the primary tumor was surgically excised and treatment was initiated. The mice were monitored at least twice a week for local tumor recurrence and for the appearance of palpable metastases in the other breast and in the regional lymph nodes.

For vaccine preparation, tumor cells were detached from the culture flasks with EDTA (Sigma Chemical Co., St Louis, Mo.), and subjected to γ-irradiation (2500 cGy from a $^{137}$Cs source), except where indicated. Haptenization was performed by the addition of 2,4-dinitrofluorobenzene (DNFB, Sigma Chemicals Co., St. Louis, Mo.) with incubation for 30 min at room temperature to prepare clinical vaccines from human tumors. For fresh DNP-modified, γ-irradiated, tumor cell vaccine the cells were used on the day of the preparation. For the frozen DNP-modified, γ-irradiated, tumor cell vaccine, the DNP-modified, γ-irradiated, tumor cells were washed and re-suspended in Hank's solution supplemented with 8% sucrose and 10% human serum albumin (HSA). The DNP-modified cells were then aliquoted, and the vials were placed into a Nalgene Cryo 1° C. Containers containing isopropanol and placed into a −80° C. freezer overnight. The frozen cells were then stored until use. Immediately prior to use, the cells were thawed in a 37° C. water bath and washed twice in Hanks' solution to remove residual HSA. Frozen unmodified, γ-irradiated, tumor cell vaccine was prepared in the same fashion, except that no DNP modification was performed. Each vaccine was administered in a total volume of 0.2 ml and consisted of $5\times10^6$ frozen DNP-modified tumor cells or unmodified tumor cells, or $3\times10^6$ fresh DNP-modified tumor cells admixed with $0.5\times10^6$ to $4\times10^6$ colony-forming units (CFU) of Bacille Calmette-Guerin (BCG, Tice strain, Oreg.).

According to the experimental design, three to five days after surgical excision of the primary rumor, the mice were given an i.p. injection of 15 mg/kg cyclophosphamide (CY; Mead Johnson—A Bristol-Myers Squibb Co., Princeton, N.J.). Three days after the low-dose CY treatment, the mice received a s.c. injection of the indicated vaccine close to the site of tumor excision. This protocol was repeated every 10 days for the duration of the experiment. As a reference points, in some experiments a group of mice received saline. All mice were monitored at least twice a week for tumor recurrence at the primary site as well as for the appearance of palpable metastases in the other breast and in the regional lymph nodes. Once metastases were evident, the progression of metastases was followed for the duration of the experiments, or until the mice showed signs of distress, after which they were sacrificed. In addition to monitoring for tumor recurrences, in some experiments, the animals were also monitored for injection site reactions and weight.

Statistical analysis of the data was conducted was conducted by plotting the fraction of animals free of tumor recurrence at each monitoring point as Kaplan-Meier type survival curves, and a log rank test was performed using GraphPad software from Prism software, San Diego, Calif. A p value of 0.05 or less was considered significant.

The results showed that frozen DNP-modified tumor cell vaccine improved relapse-free survival as compared to saline injection. A total of four experiments were carried out, each demonstrating the therapeutic benefits of the frozen DNP-modified tumor cell vaccine relative to the saline treatment group, and the results pooled. The pooled results, showing a statistically significant difference between the groups (p=0.0011) are shown in FIG. 1. Thus, treatment of mice from which the primary tumor was surgically excised with frozen DNP-modified tumor cell vaccine offers therapeutic benefits against tumor recurrence.

Figure 2:
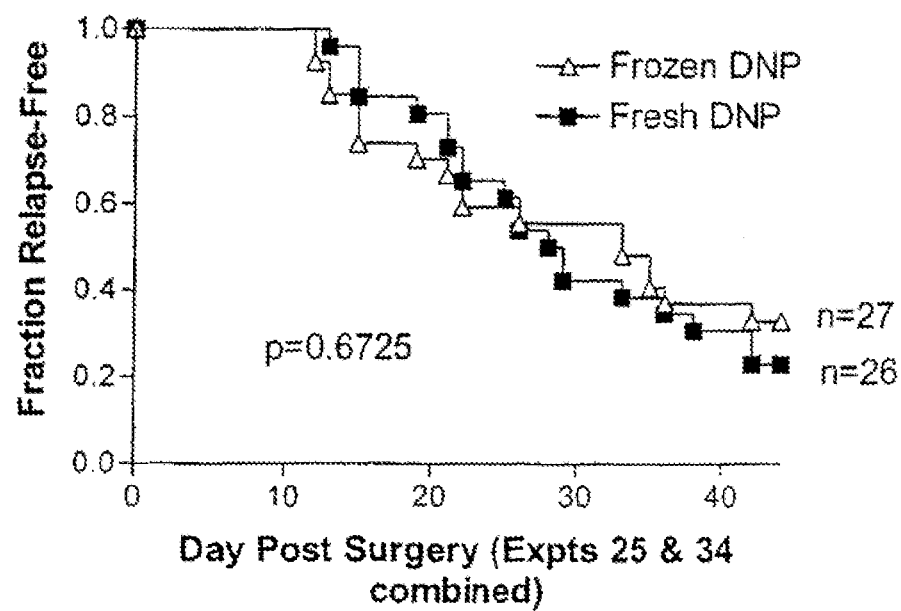
FIG. 2 shows the relapse-free survival rate of mice treated with cryogenically preserved haptenized tumor cell vaccine as compared to mice treated with fresh haptenized tumor cell vaccine.

In independent experiments, fresh and frozen DNP-modified tumor cell vaccines were compared for their therapeutic effectiveness against tumor recurrence in 410.4 tumor. When the results of the experiments were pooled, the two treatment groups offered comparable therapeutic benefits (p=0.6725). These results are displayed in FIG. 2. The therapeutic effectiveness of the frozen DNP-modified tumor cell vaccine also appeared to be similar to the therapeutic effectiveness of the fresh DNP-modified tumor cell vaccine reported by Sojka et al., (Cancer Immunol. Immunother. 2002; 51:200-208).

Figure 3:
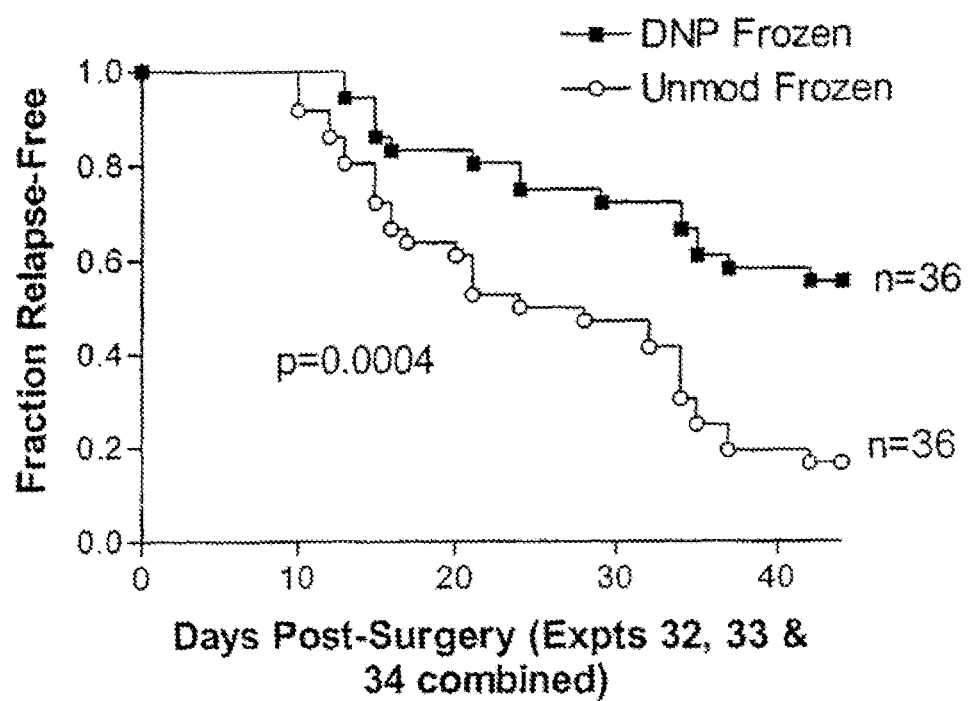
FIG. 3 shows the relapse-free survival rate of mice treated with cryogenically preserved haptenized tumor cell vaccine as compared to mice treated with cryogenically preserved non-haptenized tumor cell vaccine.

In addition to comparing the relapse-free survival of mice receiving frozen DNP-modified tumor cell vaccine to that of the saline treatment group, experiments were carried out to compare the relapse-free survival of mice receiving frozen DNP-modified irradiated tumor cell vaccine to that of mice receiving frozen unmodified irradiated tumor cell vaccine. When al studies were pooled, the DNP-modified frozen vaccine induced significantly better relapse-free survival (p=0.0004). These results are shown in FIG. 3. Taken together, our current results show that frozen DNP-modified irradiated tumor cell vaccine, like fresh DNP-modified irradiated tumor cell vaccine, is superior to unmodified irradiated tumor cell vaccine in improving the relapse-free survival of mice from which the primary 410.4 tumor was surgically excised, implying that DNP modification is essential to producing optimal anti-tumor effects.

Figure 4:
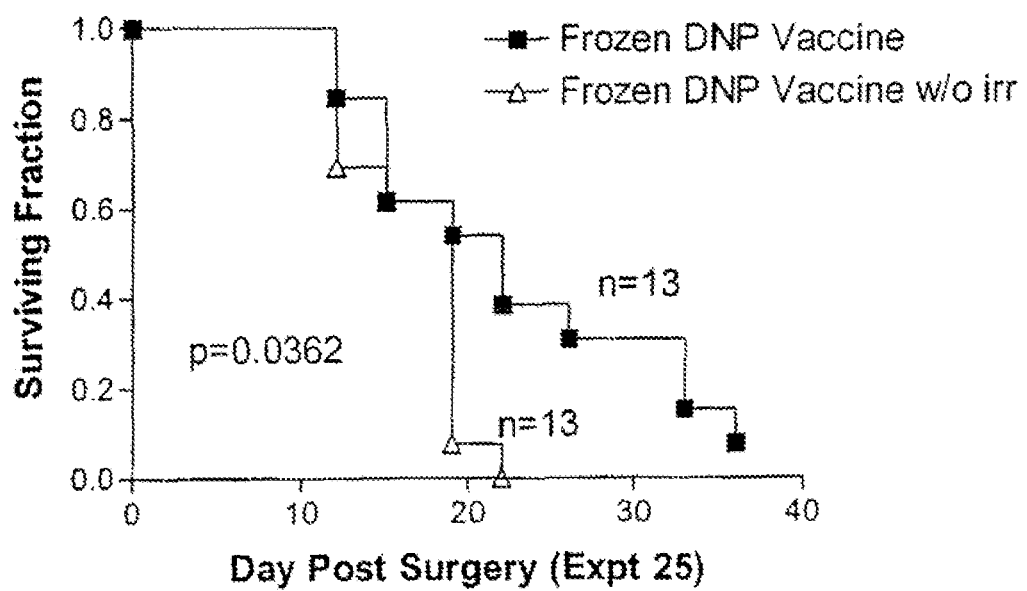
FIG. 4 shows the relapse-free survival rate of mice treated with cryogenically preserved haptenized irradiated tumor cell vaccine as compared to mice treated with cryogenically preserved haptenized non-irradiated vaccine.

Further, experimental results indicated that irradiation was important to the effect of DNP-modified tumor cell vaccine. Haptenization with DNP, with or without irradiation, has been shown to be sufficient to eliminate both in vitro proliferation and in vivo tumorigenicity. To examine whether this might allow for elimination of the irradiation step, frozen DNP-modified tumor cell vaccines prepared with or without irradiation were compared. The results indicated a significantly lower relapse-free survival for non-irradiated than frozen DNP-modified irradiated tumor cell vaccine (FIG. 4; p=0.0362). The mechanism(s) through which irradiation is improving the efficacy of DNP-modified tumor cell vaccine against tumor recurrence in the 410.4 tumor system remains to be elucidated. Irradiation has, however, been shown to activate the expression of genes (e.g., B7-1 (Morel et al., Cancer Immunol Immunother 1998; 46:277-282; Sojka et al., J Immunol 2000; 164:6230-6236; Vereecque et al., Br J. Haematol 2000; 108:825-831) and TNF-α (Hallahan et al., Proc. Natl. Acad. Sci. (USA) 1989; 86:10104-10107; Weill et al. J Interferon Cytokine Res 1996; 16:395-402)) that are known to be important for the acquisition of tumor eradicating immunity (Chen et al., Immunol Today 1993; 14:483-

486; Allison et al., Curr Opin Immunol 1995; 7:682-686; Gorelik et al., J Immunol 1995; 154:3941-3951; Sojka et al., Cancer Immunol. Immunother. 2002; 51:200-208), which might explain these results.

Finally, the DNP-modified tumor cells vaccines, whether fresh or frozen, were well tolerated. Animals that has received frozen DNP-modified irradiated tumor cell vaccine maintained their weight in a similar fashion to control animals that received saline. The only vaccine-related adverse reactions noted in these studies were edema and induration at the injection site, most likely associated with the BCG component of the vaccine. These were mild and self-limited and disappeared before the subsequent vaccination.

Example 6

Cryopreserved Bi-Haptenized Cells

This Example describes the cell recovery, antigenicity, and hapten retention of bi-haptenized melanoma cells when treated with sucrose freezing medium, comprised of sucrose, human serum albumin and Hank's buffered solution and stored in liquid nitrogen for up to 6 months.

Bi-haptenized melanoma cell compositions were prepared by conjugating approximately half of a tumor cell preparation with DNP, and the other half with SA, as described above. The sucrose freezing medium was prepared by mixing 60 ml HBSS with 40 ml 25% HSA and 8 g sucrose until the sucrose was completely dissolved, followed by sterile-filtration into a disposable plastic bottle using a 0.2 μm filter apparatus. Stability testing by cell counting and flow cytometry was essentially conducted as described in Example 3, testing for expression of the cell markers HLA Class I, CD45, GD3, S100, HMB45, and Mart-1. Tables 5 and 6 below show the results of the evaluation for 12 samples, denoted #1-12, each representing a different tumor cell preparation. In essence, there were no consistent changes in the cryopreserved cell preparations for up to 6 months of storage.

TABLE 5

Stability of Mixed Haptenized Vaccine - Cell Counts

| # | # Large Cells/Vial | Time Frozen | Cell Counts* Large | Small |
|---|---|---|---|---|
| 1 | 2.5 | 1 D | 3.4 | 4.6 |
|  |  | 2 W | 3.6 | 7.3 |
|  |  | 2 M | 2.4 | 5.6 |
|  |  | 4 M | 2.1 | 4.5 |
|  |  | 6 M | 1.5 | 5.4 |
| 2 | 2.5 | 1 D | 3.7 | 0.7 |
|  |  | 2 W | 3.3 | 0.3 |
|  |  | 2 M | 1.6 | 0.4 |
|  |  | 4 M | 1.7 | 0.4 |
|  |  | 6 M | 1.2 | 0.4 |
| 3 | 5 | 1 D | 2.5 | 0.4 |

TABLE 5-continued

Stability of Mixed Haptenized Vaccine - Cell Counts

| # | # Large Cells/Vial | Time Frozen | Cell Counts* Large | Small |
|---|---|---|---|---|
|  |  | 2 W | 2.3 | 0.2 |
|  |  | 2 M | 2.1 | 0.4 |
|  |  | 4 M | 2.6 | 0.4 |
|  |  | 6 M | 2.2 | 0.2 |
| 4 | 2.5 | 1 D | 2.5 | 0 |
|  |  | 2 W | 1.1 | 0.1 |
|  |  | 1 M | 2.4 | 0.1 |
|  |  | 2 M | 2.6 | 0.2 |
|  |  | 3 M | 2.2 | 0 |
| 5 | 1.25 | 1 D | 0.9 | 0.1 |
|  |  | 2 W | 1.7 | 0 |
|  |  | 1 M | 1.1 | 0.1 |
|  |  | 2 M | 1.3 | 0.2 |
|  |  | 3 M | 2.1 | 0.3 |
| 6 | 1.25 | 1 D | 1 | 0 |
|  |  | 2 W | 0.9 | 0.1 |
|  |  | 1 M | 1.1 | 0 |
|  |  | 2 M | 1.3 | 0.1 |
|  |  | 3 M | 0.7 | 0 |
| 7 | 2.5 | 1 D | 1.9 | 3.2 |
|  |  | 2 W | 2.4 | 3.4 |
|  |  | 1 M | 2.8 | 2.6 |
|  |  | 2 M | 2.6 | 1.8 |
|  |  | 3 M | 2.3 | 3.6 |
|  |  | 6 M | 1.3 | 2 |
| 8 | 2.5 | 1 D | 2.8 | 9.3 |
|  |  | 2 W | 3.1 | 9.4 |
|  |  | 1 M | 2.5 | 6 |
|  |  | 2 M | 2 | 8.7 |
|  |  | 3 M | 2.3 | 6.1 |
|  |  | 6 M | 2.9 | 7.2 |
| 9 | 1.25 | 1 D | 2.5 | 23 |
|  |  | 2 W | 1.6 | 11.5 |
|  |  | 1 M | 1.2 | 17.3 |
|  |  | 2 M | 1.8 | 18.3 |
|  |  | 3 M | 1.7 | 11.7 |
|  |  | 6 M | 1.7 | 11 |
| 10 | 1.25 | 1 D | 1.3 | 7.6 |
|  |  | 2 W | 1 | 6.9 |
|  |  | 1 M | 1.1 | 5.2 |
|  |  | 2 M | 1.5 | 9.7 |
|  |  | 3 M | 1.4 | 5.5 |
|  |  | 6 M | 0.6 | 5.1 |
| 11 | 1.25 | 1 D | 1.9 | 0.6 |
|  |  | 2 W | 1 | 0.8 |
|  |  | 1 W | 0.8 | 1.1 |
|  |  | 2 M | 1 | 1.1 |
|  |  | 3 M | 1.4 | 0.7 |
|  |  | 6 M | 1.2 | 0.8 |
| 12 | 1.25 | 1 D | 1.6 | 6.5 |
|  |  | 2 W | 1.1 | 5.8 |
|  |  | 6 W | 1 | 4.3 |
|  |  | 8 W | 1.4 | 6.2 |
|  |  | 3 M | 1.5 | 6.4 |
|  |  | 6 M | 0.5 | 4.7 |

*all cell counts expressed in millions
D = Day(s); W = Week(s); M = Month(s)

TABLE 6A

Stability of Mixed Haptenized Vaccine - Retention of HLA Class I, CD45, GD3, and S100 Antigens

| # | Time Frozen | HLA Class I % (+)# | Peak@ | CD45 % (+) | Peak | GD3 % (+) | Peak | S100 % (+) | Peak |
|---|---|---|---|---|---|---|---|---|---|
| 1 | 1 D | 54.4 | 5.6 | 41.1 | 4.4 | 54.5 | 5.2 | 25.8 | 5.8 |
|  | 4 M | 44.1 | 2.3 | 15.1 | 2.5 | 26.8 | 2.5 | 21.2 | 2.5 |
|  | 6 M | 69.0 | 2.0 | 42.8 | 1.9 | 38.9 | 2.0 | 42.3 | 1.9 |

TABLE 6A-continued

Stability of Mixed Haptenized Vaccine - Retention of HLA Class I, CD45, GD3, and S100 Antigens

| # | Time Frozen | HLA Class I % (+)# | Peak@ | CD45 % (+) | Peak | GD3 % (+) | Peak | S100 % (+) | Peak |
|---|---|---|---|---|---|---|---|---|---|
| 2 | 1 D | 10.8 | 3.8 | 9.5 | 4.2 | 65.9 | 8.0 | 58.7 | 4.4 |
|   | 4 M | 13.4 | 1.5 | 6.3 | 1.5 | 46.2 | 1.5 | 58.0 | 2.2 |
|   | 6 M | 12.9 | 2.2 | 7.8 | 2.3 | 68.7 | 4.2 | 62.9 | 2.2 |
| 3 | 1 D | 14.0 | | | | | | | |
|   | 4 M | 15.2 | 2.1 | 6.8 | 1.8 | 93.9 | 20.1 | 69.0 | 2.2 |
|   | 6 M | 13.1 | 2.3 | 2.8 | 2.1 | 89.7 | 11.1 | 53.9 | 2.1 |
| 4 | 1 D | 62.1 | 4.3 | 5.8 | 3.7 | 98.3 | 34.2 | 93.0 | 6.1 |
|   | 1 M | 40.9 | 2.9 | 5.8 | 3.0 | 96.9 | 16.1 | 89.2 | 9.4 |
|   | 3 M | 56.8 | 2.5 | 5.5 | 1.8 | 97.9 | 17.3 | 89.9 | 4.2 |
| 5 | 1 D | 30.2 | 4.9 | 2.3 | 5.9 | 86.1 | 38.4 | 73.7 | 5.1 |
|   | 1 M | 33.8 | 2.5 | 3.4 | 2.2 | 96.1 | 32.1 | 83.7 | 4.2 |
|   | 3 M | 34.9 | 2.8 | 2.8 | 1.9 | 90.6 | 22.0 | 88.1 | 5.2 |
| 6 | 1 D | 69.6 | 1.6 | 9.9 | 0.7 | 93.6 | 21.8 | 97.0 | 31.8 |
|   | 1 M | 58.9 | 1.8 | 4.3 | 0.6 | 92.5 | 16.1 | 93.7 | 24.3 |
|   | 3 M | 59.3 | 2.8 | 4.7 | 1.2 | 97.7 | 41.7 | 85.7 | 7.9 |
| 7 | 1 D | 43.3 | 219.0 | 26.9 | 1.4 | 42.0 | 8.6 | 54.2 | 4.9 |
|   | 2 W | 35.2 | 3.8 | 17.5 | 3.2 | 80.3 | 17.4 | 52.8 | 3.6 |
|   | 1 M | 25.4 | 2.3 | 11.2 | 2.2 | 23.1 | 7.1 | 43.6 | 3.0 |
|   | 2 M | 40.4 | 2.4 | 21.1 | 2.5 | 80.3 | 2.7 | 84.5 | 5.2 |
|   | 3 M | 76.1 | 0.9 | 34.4 | 3.7 | 90.3 | 10.5 | 98.7 | 4.4 |
|   | 6 M | 38.7 | 1.9 | 48.2 | 1.7 | 44.1 | 5.6 | 53.3 | 2.8 |
| 8 | 1 D | 24.8 | 4.0 | 11.9 | 3.8 | 38.1 | 4.6 | 39.2 | 4.3 |
|   | 2 W | 18.0 | 6.4 | 14.6 | 6.7 | 57.3 | 7.2 | 48.3 | 6.8 |
|   | 1 M | 26.6 | 2.3 | 16.6 | 2.2 | 51.7 | 2.5 | 60.7 | 2.2 |
|   | 2 M | 28.8 | 1.9 | 18.3 | 1.9 | 48.8 | 1.9 | 58.6 | 2.1 |
|   | 3 M | 56.2 | 1.6 | 58.7 | 2.4 | 78.1 | 1.8 | 87.7 | 3.2 |
|   | 6 M | 21.4 | 4.8 | 14.2 | 4.9 | 35.4 | 5.1 | 45.1 | 6.5 |
| 9 | 1 D | 87.0 | 4.1 | 89.5 | 1.6 | 71.4 | 1.3 | 48.5 | 1.0 |
|   | 1 M | 64.4 | 6.7 | 14.8 | 6.0 | 54.1 | 38.4 | 41.9 | 17.1 |
|   | 2 M | 76.6 | 6.4 | 45.8 | 3.8 | 79.1 | 6.2 | 33.2 | 3.9 |
|   | 3 M | 95.3 | 5.1 | 68.8 | 3.4 | 59.8 | 1.7 | 95.2 | 3.8 |
|   | 6 M | 55.1 | 3.2 | 29.7 | 2.5 | 38.1 | 2.5 | 28.0 | 2.7 |
| 10 | 1 D | 65.9 | 4.9 | 30.5 | 3.6 | 14.3 | 3.6 | 18.2 | 3.5 |
|   | 2 W | 66.2 | 5.2 | 53.3 | 2.3 | 47.4 | 4.1 | 22.1 | 2.2 |
|   | 1 M | 80.9 | 2.6 | 68.2 | 1.6 | 40.1 | 1.2 | 31.5 | 1.3 |
|   | 2 M | 78.1 | 3.0 | 51.1 | 2.3 | 33.6 | 1.6 | 22.7 | 1.4 |
|   | 3 M | 77.5 | 7.0 | 60.5 | 3.7 | 19.7 | 6.7 | 30.4 | 4.7 |
|   | 6 M | 81.9 | 5.3 | 43.5 | 2.1 | 33.3 | 2.2 | 35.8 | 2.1 |
| 11 | 1 D | 52.1 | 3.4 | 26.3 | 1.9 | 79.0 | 10.6 | 77.5 | 5.8 |
|   | 2 M | 39.8 | 1.9 | 17.8 | 2.1 | 98.4 | 19.6 | 96.0 | 10.3 |
|   | 3 M | 55.2 | 0.9 | 20.7 | 3.4 | 95.3 | 3.1 | 98.7 | 6.8 |
|   | 6 M | 38.8 | 1.7 | 37.6 | 1.2 | 86.3 | 8.6 | 83.3 | 4.8 |
| 12 | 1 D | 67.1 | 2.7 | 55.2 | 2.6 | 79.6 | 4.6 | 68.7 | 3.7 |
|   | 6 W | 62.1 | 2.5 | 36.6 | 2.2 | 39.7 | 1.8 | 41.6 | 2.3 |
|   | 8 W | 66.6 | 3.0 | 35.1 | 2.2 | 51.2 | 1.8 | 57.7 | 2.6 |
|   | 3 M | 81.9 | 2.2 | 33.3 | 1.2 | 45.6 | 1.0 | 81.4 | 3.6 |
|   | 6 M | 77.3 | 4.6 | 57.8 | 2.6 | 49.7 | 3.2 | 62.3 | 3.5 |

% (+) indicates the percentage of cells expressing the marker
@Peak indicates peak fluorescence channel of positive cells
D = Day(s); W = Week(s); M = Month(s)

TABLE 6B

Stability of Mixed Haptenized Vaccine - Retention of HMB45, MART-1 Antigens, and DNP and SA Haptens

| # | Time Frozen | HMB45 % (+) | Peak | MART-1 % (+) | Peak | DNP % (+) | Peak | SA % (+) | Peak |
|---|---|---|---|---|---|---|---|---|---|
| 1 | 1 D | 5.4 | 4.6 | 11.0 | 33.6 | 53.9 | 16.2 | 55.3 | 4.1 |
|   | 4 M | 1.5 | 2.9 | 12.7 | 3.2 | 52.1 | 7.1 | 22.2 | 3.2 |
|   | 6 M | 2.3 | 2.5 | 10.3 | 2.2 | 56.6 | 5.6 | 33.4 | 2.3 |
| 2 | 1 D | 6.4 | 3.2 | 12.7 | 3.4 | 60.6 | 35.1 | 34.4 | 3.5 |
|   | 4 M | 6.0 | 1.8 | 9.9 | 1.5 | 56.6 | 6.4 | 30.0 | 7.3 |
|   | 6 M | 8.4 | 2.1 | 14.3 | 3.0 | 63.1 | 12.5 | 27.7 | 12.0 |
| 3 | 4 M | 13.3 | 1.8 | 14.2 | 1.8 | 71.0 | 18.0 | 34.1 | 1.9 |
|   | 6 M | 11.3 | 2.0 | 4.4 | 2.0 | 82.6 | 18.2 | 21.8 | 12.9 |
| 4 | 1 D | 2.2 | 3.8 | 3.0 | 4.0 | 63.1 | 35.4 | 41.2 | 35.7 |
|   | 1 M | 2.6 | 3.4 | 1.7 | 2.9 | 62.4 | 34.5 | 34.5 | 8.1 |
|   | 3 M | 3.8 | 2.0 | 3.7 | 2.0 | 65.7 | 32.1 | 37.1 | 8.6 |
| 5 | 1 D | 8.0 | 5.3 | 30.9 | 5.5 | 63.1 | 37.7 | 41.8 | 11.8 |
|   | 1 M | 8.3 | 3.4 | 38.1 | 3.0 | 59.1 | 26.6 | 40.1 | 4.7 |
|   | 3 M | 6.6 | 1.7 | 43.1 | 2.8 | 54.0 | 11.6 | 42.1 | 6.9 |
| 6 | 1 D | 84.8 | 1.0 | 54.9 | 1.7 | 48.7 | 8.2 | 41.5 | 32.1 |
|   | 1 M | 71.1 | 1.4 | 42.8 | 0.9 | 44.8 | 4.2 | 44.7 | 30.1 |
|   | 3 M | NA | NA | 44.2 | 2.5 | 43.7 | 5.8 | 40.2 | 20.5 |
| 7 | 1 D | 1.5 | 1.6 | 2.2 | 1.4 | 47.0 | 8.7 | 27.1 | 3.1 |

TABLE 6B-continued

Stability of Mixed Haptenized Vaccine - Retention
of HMB45, MART-1 Antigens, and DNP and SA Haptens

| | Time Frozen | HMB45 % (+) | HMB45 Peak | MART-1 % (+) | MART-1 Peak | DNP % (+) | DNP Peak | SA % (+) | SA Peak |
|---|---|---|---|---|---|---|---|---|---|
| | 2 W | 3.2 | 3.2 | 1.6 | 3.2 | 51.4 | 29.3 | 54.7 | 8.7 |
| | 1 M | 1.8 | 2.3 | 6.2 | 2.5 | 54.2 | 7.9 | 32.8 | 4.0 |
| | 2 M | 2.4 | 2.1 | 1.7 | 2.1 | 54.3 | 20.5 | 55.5 | 5.0 |
| | 3 M | 7.3 | 0.7 | 7.4 | 0.8 | 54.5 | 14.9 | 59.1 | 3.8 |
| | 6 M | 2.3 | 1.9 | 1.5 | 2.3 | 56.3 | 11.0 | 35.7 | 4.5 |
| 8 | 1 D | 1.4 | 3.4 | 7.5 | 3.4 | 43.8 | 7.0 | 23.2 | 3.8 |
| | 2 W | 2.9 | 7.0 | 17.0 | 6.8 | 52.3 | 12.6 | 25.4 | 8.0 |
| | 1 M | 2.9 | 2.4 | 10.5 | 2.3 | 54.1 | 6.4 | NA | NA |
| | 2 M | ND | ND | 9.7 | 2.0 | 52.0 | 10.0 | 35.4 | 2.5 |
| | 3 M | 4.3 | 1.4 | 23.3 | 4.1 | 55.3 | 12.1 | 46.4 | 7.7 |
| | 6 M | 3.9 | 5.2 | 9.3 | 5.0 | 45.2 | 6.7 | 23.8 | 6.2 |
| 9 | 1 D | 3.6 | 0.9 | 2.4 | 1.1 | 42.5 | 9.1 | 51.8 | 2.7 |
| | 1 M | 0.7 | 5.9 | 16.9 | 6.3 | 53.3 | 28.0 | 57.1 | 18.9 |
| | 2 M | 1.9 | 4.0 | 17.8 | 6.1 | 54.2 | 12.0 | 62.5 | 7.0 |
| | 3 M | | | 20.3 | 6.4 | 57.1 | 16.2 | 66.2 | 4.2 |
| | 6 M | 1.3 | 2.3 | 11.2 | 4.6 | 51.4 | 8.4 | 61.5 | 1.5 |
| 10 | 1 D | 0.9 | 3.8 | 1.7 | 3.5 | 61.5 | 14.7 | 39.9 | 10.4 |
| | 2 W | 1.6 | 2.5 | 4.2 | 2.3 | 58.9 | 10.6 | 83.4 | 6.5 |
| | 1 M | 3.5 | 1.3 | 3.6 | 1.2 | 60.9 | 7.0 | 39.2 | 1.9 |
| | 2 M | 1.9 | 1.4 | 2.8 | 1.4 | 60.9 | 5.8 | 42.6 | 2.4 |
| | 3 M | 1.6 | 4.5 | 4.4 | 4.3 | 70.6 | 13.8 | 41.9 | 6.6 |
| | 6 M | 3.2 | 2.4 | 2.2 | 2.7 | 69.7 | 7.6 | 28.3 | 2.6 |
| 11 | 1 D | 23.9 | 2.0 | 28.6 | 2.4 | 45.7 | 23.4 | 36.0 | 20.1 |
| | 2 M | 21.9 | 1.8 | 23.7 | 2.0 | 52.6 | 21.4 | 44.5 | 34.5 |
| | 3 M | NA | NA | 42.0 | 1.9 | 52.5 | 30.4 | 67.3 | 33.3 |
| | 6 M | 13.4 | 1.7 | 14.6 | 1.6 | 48.9 | 13.4 | 42.0 | 25.2 |
| 12 | 1 D | 2.1 | 2.2 | 9.3 | 2.5 | 56.8 | 13.1 | 44.7 | 4.2 |
| | 6 W | 3.7 | 1.7 | 23.1 | 16.3 | 62.6 | 6.7 | 36.4 | 1.7 |
| | 8 W | 5.1 | 1.9 | 18.7 | 25.2 | 67.0 | 5.5 | 41.3 | 1.9 |
| | 3 M | NA | NA | 28.2 | 5.9 | 63.7 | 5.1 | 26.7 | 2.1 |
| | 6 M | 3.1 | 2.3 | 24.9 | 10.0 | 58.3 | 8.5 | 33.2 | 2.3 |

% (+) indicates the percentage of cells expressing the marker
@ Peak indicates peak fluorescence channel of positive cells
D = Day(s) W = Week(s); M = Month(s)

Example 7

Clinical Studies with Cryopreserved Cells

This Example outlines various clinical studies using freezing medium treated cryopreserved haptenized cells.

A novel human cancer vaccine, consisting of autologous tumor cells modified with the hapten, dinitrophenyl (DNP), has been developed. The DNP-modified vaccine induces unique immunological effects and shows clinical efficacy. A second-generation vaccine composed of autologous tumor cells, half of which have been modified with DNP and half with a second hapten, sulfanilic acid (SA), has also been developed. This "bihaptenized" vaccine is immunologically more potent and clinically more effective.

A phase I trial of the bihaptenized vaccine in patients with stage IV melanoma is conducted, testing four dosage levels. The major endpoints are the development of delayed-type hypersensitivity (DTH) to DNP-modified, SA-modified, and unmodified autologous tumor cells. Also, the development of tumor inflammatory responses is studied.

Subsequently, a phase II trial using the lowest dose that is found to be immunologically effective in the phase I trial is conducted. The immunological basis of a newly discovered phenomenon—the importance of the timing of a vaccine "induction" dose, is investigated. The hypothesis that the administration of an induction dose timed optimally with administration of low dose cyclophosphamide results in selective depletion of suppressor T cells that would otherwise down-regulate or abrogate the anti-tumor immune response is tested. Peripheral blood lymphocytes are obtained from patients at various time points and assayed for the presence of suppressor cells. It is then determined whether such suppressor cells have a characteristic phenotype, $CD4^+CD25^+$ with co-expression of CTLA4, and whether upon stimulation they produce the immunoregulatory cytokine, IL10. Finally, the ability of the suppressor cells to down-regulate in vitro T cell responses to alloantigens, hapten-modified tumor cells, and unmodified tumor cells, is tested. These studies provide insights into the immunobiology of human cancer vaccines and assist in the development of more effective immunotherapy strategies.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are to some degree approximate, and are provided for purposes of description.

Patents, patent applications, publications, product descriptions, and protocols are cited throughout this application, the disclosures of which are incorporated herein by reference in their entireties.

What is claimed is:

1. A method of preserving haptenized tumor cells, which method comprises: (i) contacting the haptenized tumor cells with a freezing medium, wherein the freezing medium comprises sucrose, human serum albumin and an isotonic buffered solution; and (ii) freezing the tumor cells, whereby the immunogenicity of the tumor cells is preserved.

2. The method of claim 1, wherein the isotonic buffered solution is Hank's buffered solution.

3. The method of claim 1, wherein the freezing medium comprises 8% sucrose, 10% human serum albumin and the isotonic buffered solution is Hank's buffered solution.

4. The method of claim 1, wherein the cells are frozen at a temperature of from about −80° C. to about −196° C.

5. The method of claim 1, wherein the tumor cells are selected from the group consisting of melanoma cells, ovarian cancer cells, colorectal cancer cells, small cell lung cancer cells, kidney cancer cells, breast cancer cells, and leukemia cells.

6. The method of claim 5, wherein the tumor cells are melanoma cells.

7. The method of claim 1, wherein the tumor cells are haptenized with at least one hapten selected from the group consisting of DNP, TNP, and sulfanilic acid.

8. The method of claim 5, wherein the tumor cells are haptenized with DNP.

9. The method of claim 7, wherein the tumor cells are haptenized with at least two different haptens.

10. The method of claim 1, which said method further comprises storing the frozen haptenized tumor cells and a freezing medium for at least 3 months.

11. The method of claim 10, wherein the cells are frozen at a temperature of from about −80° C. to −196° C.

12. The method of claim 5, wherein the tumor cells are haptenized with at least one hapten selected from DNP and sulfanilic acid.

\* \* \* \* \*